United States Patent
Stephanopoulos et al.

(10) Patent No.: US 7,531,345 B2
(45) Date of Patent: May 12, 2009

(54) MUTATIONS FOR ENHANCED TYROSINE PRODUCTION

(75) Inventors: Gregory Stephanopoulos, Winchester, MA (US); Tina Lutke-Eversloh, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/434,523

(22) Filed: May 16, 2006

(65) Prior Publication Data

US 2007/0065910 A1 Mar. 22, 2007

Related U.S. Application Data

(60) Provisional application No. 60/681,142, filed on May 16, 2005.

(51) Int. Cl.
*C12P 13/22* (2006.01)
*C12N 1/20* (2006.01)
*C12N 1/00* (2006.01)
*C07H 21/04* (2006.01)

(52) U.S. Cl. ............ 435/252.3; 435/320.1; 435/252.31; 435/252.33; 435/254.2; 435/254.21; 536/23.2

(58) Field of Classification Search ................ None
See application file for complete search history.

(56) References Cited

U.S. PATENT DOCUMENTS 7,238,855 B2 * 7/2007 Valentin et al. ............. 800/281

OTHER PUBLICATIONS

Whisstock, et al. Quarterly Rev. Biophy. 2003, 36, pp. 307-340.*

* cited by examiner

*Primary Examiner*—Nashaat T Nashed
*Assistant Examiner*—MD. Younus Meah
(74) *Attorney, Agent, or Firm*—Pearl Cohen Zedek Latzer, LLP; Mark S. Cohen

(57) ABSTRACT

The present invention provides cells genetically engineered to express mutated chorismate mutase/prephenate dehydrogenase (CM/PDH), the nucleic acid coding for each mutated CM/PDH and similar nucleic acids and methods for utilizing cells expressing mutated CM/PDH to produce tyrosine.

11 Claims, 3 Drawing Sheets

Figure 3

```
             10        20        30        40        50        60        70        80        90
100
        ....|....|....|....|....|....|....|....|....|....|....|....|....|....|....|....|....|....|....|
WT      MVAELTALRDQIDEVDKALLNLLAKRLELVAEVGEVKSRFGLPIYVPEREASMLASRRAEAEALGVPPDLIEDVLRRVMRESYSSENDKGFKTLCPSLRP
5       MVAELTALRDQIDEVDKALLNLLAKRLELVAEVGEVESRFGLPIYVSEREASMLASRRAEAEALGVPPDLIEDVLRRVMRESYSSENDKGFKTLCPSLRP
7       MVAELTALRDRIDEVDKALLNLLAKRLELAAEVGEVKSRFGLPIYVPEREASMLASRRAEAEALGVPPDLIEDVLRRVMRESYSSENDKGFKTLCPSLRP
10      MVAELTALRDQIDEVDKALLNLLAKRLELVAEVGEAKSRFGLPIYVPEREAPMLASRRAEAEALGVPPDLIEDVLRRVMRESYSSENDKGFKTLCPSLRP
13      MVAELTALRDQIDEVDKALLNLLAKRLELVAEVGEVKGRFGLPIYVPEREASMLASRRAEAEALGVPPDLIEDVLRRVMRESYSSENDKGFKTLCPSLRP
15      MVAELTALRDQVDEVDKALLNLLAKRLELVAEVGEVKSRFGLPIYVPEREASMLASRRAEAEALGVPPDLIEDVLRRVMRESYSSENDKGFKTLCPSLRP
18      MVAELTALRDQIDEVDKALLNLLAKRLELVAEVGEVKSRFGLPIYVPEREASMLASRRAEAEALGVPPDLIEDVLRRVMRESYSSENDKGFKTLCPSLRP
20      MVAELTALRDQIDEVDKALLNLLAKRLELVAEVGEVKSRFGLPIYVPEREASILASRRAEAEALGVPPDLIEDVLRRVMRESYSSENDKGFKTLCPSLRP 110       120       130       140       150       160       170       180       190
200
        ....|....|....|....|....|....|....|....|....|....|....|....|....|....|....|....|....|....|....|
WT      VVIVGGGQMGRLFEKMLTLSGYQVRILEQHDWDRAADIVADAGMVIVSVPIHVTEQVIGKLPPLPKDCILVDLASVKNGPLQAMLVAHDGPVLGLHPMF
5       VVIVGGGQMGRLFEKMLTLSGYQVRILEQHDWDRAADIVADAGMVIVSVPIHVTEQVIGKLPPLPKDCILVDLASVKNRPLQAMLVAHGGPVLGLHPMF
7       VVIVGGGQMGRLFEKMLTLSGYRVRILEQHDWDRAADIVADAGMVIVSVPIHVTEQVIGKLPPLPKDCILVDLASVKNGPLQAMLVAHDGPVLGLHPMF
10      VVIVGGGQMGRLFEKMLTLSGYQVRILEQHDWDRAADIVADAGMVISVPIHVTEQVIGKLPPLPKDCILVDLASVKNGPLQAMLVAHDGPVLGLHPMF
13      VVIVGGGQMGRLFEKMLTLSGYQVRILEQHDWDRAADIVADAGMVIVSVPIHVTERVIGKLPPLPKDCILVDLASVKNGPLQAMLVAHDGPVLGLHPMF
15      VVIVGGGQMGRLFEKMLTLSGYQVRILEQHDWDRAADIVADAGMVIVSVPIHVTEQVIGKLPPLPKDCILVDLASVKNGPLQAMLVAHDGPVLGLHPMF
18      VIIVGGGQMGRLFEKMLTLSGYQVRILEQHDWDRAADIVADAGMVIVSVPIHVTEQVDKLPPLPKDCILVDLASVKDGPLQAMLVAHDGPVLGLHPMF
20      VVIVGGGQMGRLFEKMLTLSGYQVRILEQHDWDRAADIVADAGMVIVSVPIHVTEQVIGKLPPLPKDCILVDLASVKNGPLQAMLVAHDGPVLGLHPMF 210       220       230       240       250       260       270       280       290
300
        ....|....|....|....|....|....|....|....|....|....|....|....|....|....|....|....|....|....|....|
WT      GPDSGSLAKQVVVWCDGRKPEAYQWFLEQIQVWGARLHRISAVEHDQNMAFIQALRHFATFAYGLHLAEENVQLEQLLALSSPIYRLELAMVGRLFAQDP
5       GPDSGSLAKQVVVWCDGRKPEAYQWFLEQIQVWGARLHRISAVEHDQNMAFIQALRHFATFAYGLHLAEENVQLEQLLALSSPIYRLELAMVGRLFAQDP
7       GPDSGSLAKQVVVWCDGRKPEAYQWFLEQIQVWGARLHRISAVEHDQNMAFIQALRHFATFAHGLHLAEENVQLEQLLALSSPIYRLELAMVGRLFAQDP
10      GPDSGSLAKQVVVWCDGRKPEAYQWFLEQIQVWGARLHRISAVEHDQNMAFIQALRHFATFAYGLHLAEENVQLEQLLALSSPIYRLELAMVGRLFAQDP
13      GPDSGSLAKQVVVWCDGRKPEAYQWFLEQIQVWGARLHRISAVEHDQNMAFIQALRHFATFAHGLHLAEENVQLEQLLALSSPIYRLELAMVGRLFAQDP
15      GPDSGSLAKQVVVWCDGRKPEAYQWFLEQIQVWGARLHRISAVEHDQNMAFIQALRHFATFAYGLHLAEENVRLEQLLALSSPIYRLELAMVGRLFAQDP
18      GPDSGSLAKQVVVWCDGRKPEAYQWFLEQIQVWGARLHRISAVEHDQNMAFIQALRHFATFAYGLHLAEENVQLEQLLALSSPIYRLELTMVGRLFAQDP
20      GPDSGSLAKQVVVWCDGRKPEAYQWFLEQIQVWGARLHRISAVEHDQNMAFIQALRHFATFAYGLHLAEENVQLEQLLALSSPIYRLELAMVGRLFAQDP 310       320       330       340       350       360       370
        ....|....|....|....|....|....|....|....|....|....|....|....|....|....
WT      QLYADIIMSSERNLALIKRYYKRFGEAIELLEQGDKQAFIDSFRKVEHWFGDYAQRFQSESRVLLRQANDNRQ*
5       QLYADIIMSSERNLALIKRYYKRLGEAIELLEQGDKQAFIDSFRKVEHWFGDYAQRIQSESRVLLRQANDNRQ*
7       QLYADIIMSSERNLALIKRYYKRFGEAIELLEQGDKQAFIDSFRKVEHWFGDYAQRFQSESRVLLRQANDNRQ*
10      QLYADIIMSSERNLALIKRYYKRFGEAIELLEQGDKQAFIDSFRKVEHWFGDYAQRIQSESRVLLRQANDNRQ*
13      QLYADIIMSSERNLALIKRYYKRFGEAIELLEQGDKQAFIDSFRKVEHWFGDYAQRFQSESRVLLRQANDNRQ*
15      QLYADIIMSSERNLALIKRYYKRFGEAIELLEQGDKQAFIDSFRNVEHWFGDYAQRIQSESRVLLRQANDNRQ*
18      QLYADIIMSSERNLALIKRYYKRFGEAIELLEQGDKQAFIDSFRKVEHWFGDYAQRIQSESRVLLRQANDNRQ*
20      QLYADIIMSSERNLALIKRYYKRFGEAIELLEQGDKQAFIDSFRKVEHWFGDYVQRFQSESRVLLRQANDNRQ*
```

MUTATIONS FOR ENHANCED TYROSINE PRODUCTION

CROSS-REFERENCE TO RELATED APPLICATIONS

This Application claims the benefit of U.S. Provisional Application Ser. No. 60/681,142, filed May 16, 2005, which is hereby fully incorporated.

FIELD OF THE INVENTION

This invention is directed to mutated proteins which result in enhanced tyrosine production, constructs and cells for effecting the same, and their use in the preparation of tyrosine enriched foods and dietary supplements.

BACKGROUND OF THE INVENTION

Amino acids play a central role both as building blocks of proteins and as intermediates in metabolism. The chemical properties of the amino acids of proteins determine the biological activity of the protein, which in turn catalyze the large majority of the reactions in living cells and control virtually all cellular process.

Tyrosine is a polar and very weakly acidic aromatic amino acid. Tyrosine plays an important catalytic role in the active site of some enzymes (e.g. the bacterial enzyme DNA gyrase) and can be chemically modified after it has been incorporated into a peptide chain. A kinase enzyme (e.g. Wee1 involved in control of the cell cycle in yeast) can chemically link a phosphate group via the hydroxyl oxygen in a process called phosphorylation. The process can be reversed by a phosphatase enzyme (e.g. Cdc25 which reverses the effect of Wee1). This type of modification of tyrosine is extremely important in the regulation of the activity of various proteins.

Tyrosine is the direct precursor to several important neurotransmitters, such as dopamine, norepinephrine, epinephrine, and L-dopa. Some of the functions regulated by these tyrosine-dependent neurotransmitters include mood, stress response, mental function, satiety and sex drive. Tyrosine is also an important component of hormones that are produced by the thyroid. These hormones are in turn vital for managing metabolism. Tyrosine is also required to form melanin, the dark pigment that provides protection from the harmful effects of ultraviolet light. Dairy products, meats, fish, wheat, oats, as well as many other foods contain tyrosine.

In humans, tyrosine is a non-essential amino acid synthesized from the essential amino acid phenylalanine. Most plants and microorganisms, on the other hand, can synthesize tyrosine. The first step in the synthesis of the aromatic amino acids, including tyrosine, is the condensation of erythrose-4-phosphate and phosphoenolpyruvate to 3-deoxy-D-arabino-heptulosonic acid-7 phosphate (DAHP). In *Escherichia coli*, this reaction is carried out by three isoenzymes, aroF, aroG, and aroH.

Chorismate is a central intermediate of the shikimate pathway, and a branch point for five different metabolic pathways in microorganisms, including aromatic amino acid synthesis. Tyrosine is synthesized from chorismate via three enzymatic reactions, mediated by chorismate mutase, prephenate dehydrogenase, and transaminase A. In *E. coli*, both the CM and PDH activities are located in a single, bifunctional protein known as the T-protein, which is a homodimer with a molecular weight of approximately 78,000 that is encoded by the tyrA gene. The CM and PDH domains are located on the N- and C-terminal of TyrA, respectively.

In the first reaction, chorismate undergoes a Claisen rearrangement to form prephenate, which is catalyzed by chorismate mutase (CM). In the second reaction, prephenate undergoes NAD+-mediated oxidative decarboxylation to p-hydroxyphenylpyruvate, which is catalyzed by prephenate dehydrogenase (PDH). Finally, p-hydroxyphenylpyruvate is transaminated by transaminase A to produce L-tyrosine. Tyrosine (Tyr) is an end product inhibitor of both CM and PDH, and induces aggregation of the T-protein diminishing potential yields of this important amino acid.

SUMMARY OF THE INVENTION

The invention provides, in one embodiment, a cell engineered to express a mutated chorismate mutase/prephenate dehydrogenase (CM/PDH) protein such that CM/PDH is resistant to feedback inhibition by tyrosine.

In one embodiment, this invention provides a cell engineered to express a chorismate mutase/prephenate dehydrogenase (CM/PDH) protein, wherein the protein comprises a mutation in at least one amino acid at position 95-370 of SEQ ID No: 1 and is subject to lower or no feedback inhibition by tyrosine.

According to this aspect of the invention, and in one embodiment, the mutation comprises a substitution of a valine with an isoleucine, a glutamine with an arginine, a phenylalanine with a leucine, or a combination thereof, and in another embodiment, the mutation is at position 102, 124, 148, 157, 160, 179, 180, 190, 263, 273, 290, 324, 345, 354, 355, 357, or a combination thereof. In another embodiment, the mutation comprises a substitution of: a valine with an isoleucine at position 102, a valine with an isoleucine at position 148, a glutamine with an arginine at position 124, a glutamine with an arginine at position 157, a glutamine with an arginine at position 273, a glycine with an aspartic acid at 160, an asparagine with an aspartic acid at position 179, a glycine with an arginine at position 180, an aspartic acid with a glycine at position 190, a tyrosine with a histidine at position 263, a tyrosine with a cysteine at position 263, an alanine with a threonine at position 290, a phenylalanine with a leucine at position 324, a phenylalanine with a leucine at position 357, a lysine with an asparagine at position 345, an alanine with a valine at position 354, a glutamine with a arginine at position 355, or a combination thereof. In another embodiment, the protein has an amino acid sequence corresponding to or homologous to SEQ ID Nos: 2-21.

In another embodiment, this invention provides an isolated nucleic acid comprising a nucleotide sequence sharing at least 90% homology with the sequence as set forth in SEQ ID Nos: 22-42, wherein the nucleic acid encodes a polypeptide involved in tyrosine biosynthesis. In one embodiment, the invention provides a vector comprising a nucleic acid of this invention, or in another embodiment, a cell comprising a vector of this invention.

In another embodiment, this invention provides a method for producing tyrosine, comprising engineering a cell to express a chorismate mutase/prephenate dehydrogenase (CM/PDH) protein, wherein the protein comprises a mutation in at least one amino acid at position 95-370 of SEQ ID No: 1 in a cell comprising a gene or genes involved in the tyrosine biosynthetic pathway, culturing the cell under conditions and for a period of time whereby tyrosine is produced and isolating tyrosine from the culture.

According to this aspect of the invention, and in one embodiment, the cell enhances tyrosine production by 0.25-10-fold when in the presence of tyrosine, and in another embodiment, the cell is a bacterium or a yeast.

This invention also provides a tyrosine-enriched food or dietary supplement, prepared using a cell or nucleic acid of this invention or according to the method of this invention.

BRIEF DESCRIPTION OF THE DRAWINGS

FIG. 3 presents a comparison of the deduced amino acid sequences of seven tyrA$^{fbr}$ mutants (referred to as 5, 7, 10, 13, 15, 18, 20) with tyrA$^{WT}$ (WT) of *E. coli* K12. Amino acid substitutions found in the mutant strains are shaded.

DETAILED DESCRIPTION OF THE PRESENT INVENTION

Figure 1:
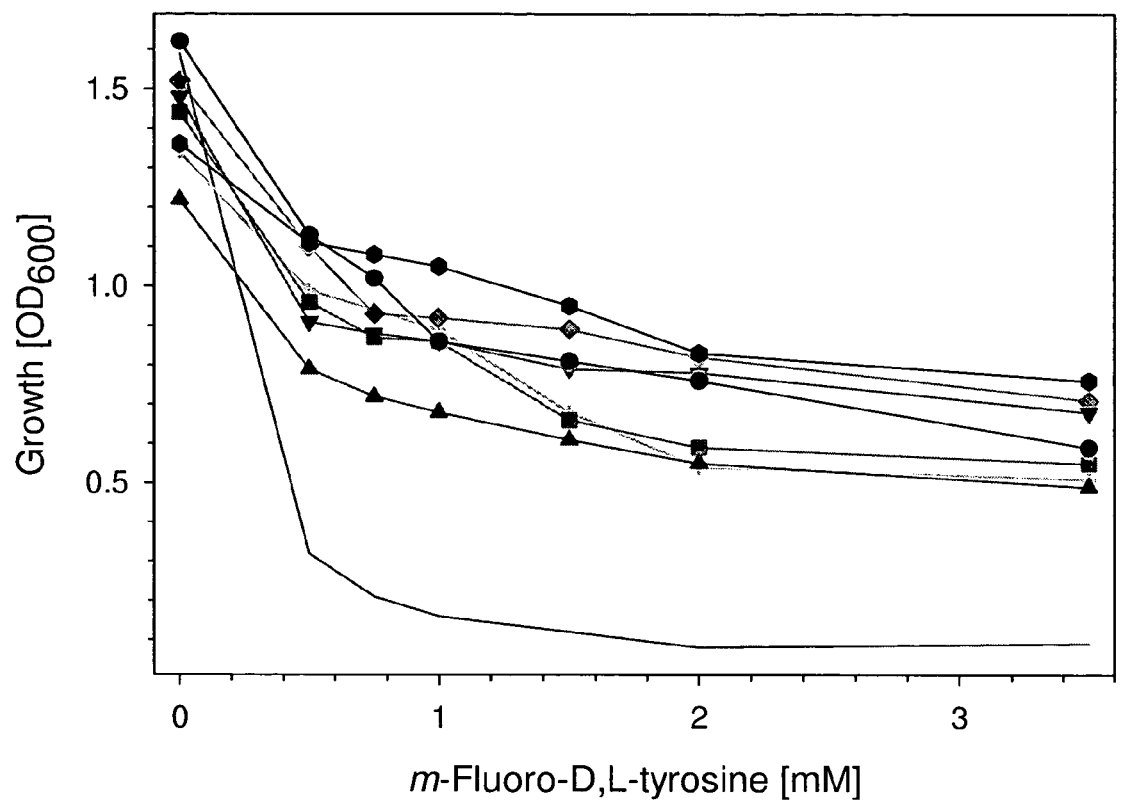
FIG. 1 demonstrates experimental results showing the effect of varying concentrations of m-fluoro-D,L-tyrosine on the growth of *E. coli* DH5α strains expressing wild type (tyrA$^{WT}$) and mutant (tyrA$^{fbr}$) genes. The growth in *E. coli* DH5α strains harboring eight different plasmids are presented: −, pZE21::tyr$^{WT}$; +, pZE21::tyrA$^{fbr-5}$; ■, pZE21::tyrA$^{fbr-7}$; ▲, pZE21::tyrA$^{fbr-10}$; ◆, pZE21::tyrA$^{fbr-13}$; ▼, pZE21::tyrA$^{fbr-15}$; ●, pZE21::tyrA$^{fbr-18}$; ●, pZE21::tyrA$^{fbr-20}$. Mutants of the tyrA gene from *E. coli* K12 were generated by error-prone PCR, cloned into pZE21-MCS1, and transformed into *E. coli* DH5α. m-fluoro-D,L-tyrosine is a tyrosine analogue which inhibits growth of *E. coli* DH5α harboring plasmid pZE21::tyrA$^{WT}$. *E. coli* cells were cultivated in MOPS-buffered minimal medium containing m-fluoro-D,L-tyrosine. After incubation at 37° C. at 225 rpm on a rotary shaker for 20 h, the optical density at 600 nm (OD$_{600}$) was measured.

In one embodiment, this invention provides a cell engineered to express a mutated chorismate mutase/prephenate dehydrogenase (CM/PDH) protein such that CM/PDH is resistant to feedback inhibition by tyrosine for the production of tyrosine-enriched food.

In one embodiment, the term "engineered to express" refers to cells that are modified to express a protein or proteins, which are not natively expressed in those cells. In one embodiment, such expression may be as a result of integration of a sequence of interest within a genome of the cell, to facilitate such expression, or, in another embodiment, specific mutation of a sequence of interest in the genome, or in another embodiment, may be a result of extrachromosomal expression, such as via a plasmid, as will be appreciated by one skilled in the art.

The cells are engineered to express a mutated chorismate mutase/prephenate dehydrogenase (CM/PDH) protein. In one embodiment, the term "mutation", "mutated", or "mutant" refers to insertion, deletion, or substitution of one or more natural or wild type nucleic acids for alternate nucleic acids, with "mutant" referring in another embodiment to the protein product, which comprises a mutated nucleic acid.

In one embodiment, the mutations are in a gene encoding a CM/PDH protein, which may be referred, in another embodiment, to a TyrA protein. Such a protein may comprise an amino acid sequence that corresponds to that set forth in Genbank Accession Nos: ZP_00134637, NP_214202, AAA20868, CAH09398, NP_885306, YP_178149, CAD83697, CAG76249, C85906, P43902, NP_860524, YP_156103, CAD00002, YP_088294, AAU92306, BAB72376, CAA42950, NP_245601, CAG21353, CAE13557, NP_791573, AAL21558, NP_716982, NP_838171, CAG43082, NP_827697, NP_898149, NP_796926, NP_791573, YP_200673, NP_779566, P20049, O60078 or CAC92518, or a homologue thereof.

In another embodiment, the mutations are of a tyrA gene, which has a nucleic acid sequence that is homologous to or corresponds to that set forth in Genbank Accession Nos: NC_000918, NC_006270, CR626927, NC_004307, BX640413, NC_006932, BX571965, AL139074, BA000036, AF318277, M74135, M10431, NC_006510, BA000045, NC_002940, NC_004917, NC_006512, X78413, NC_006087, AE011307, AL596170, NC_006300, NC_003551, NC_003901, AE017282, NC_002945, NC_005213, NC_002946, BA000019, BA000028, NC_005877, NC_005071, AE010268, NC_005027, AL627276, BX571857, CP000023, NC_003888, BX569694, BA000022, NC_002689, NC_004113, NC_005835, U62056, NC_003919, NC_003919, NC_003070, AL398945, NC_003421 or BX936398.

In one embodiment, the term "homologue" or "homology" refers to a molecule with significant sequence identity shared between the molecule and a reference sequence. In one embodiment, the term "homologue" or "homology" refers to a molecule sharing at least 70%, or in another embodiment, at least 72%, or in another embodiment, at least 75%, or in another embodiment, at least 77%, or in another embodiment, at least 80%, or in another embodiment, at least 82%, or in another embodiment, at least 85%, or in another embodiment, at least 87%, or in another embodiment, at least 90%, or in another embodiment, at least 92%, or in another embodiment, at least 94%, or in another embodiment, at least 95%, or in another embodiment, at least 97%, or in another embodiment, at least 99%, or in another embodiment, 100% identity with a reference sequence. In one embodiment, homology is in reference to a nucleic acid sequence, or in another embodiment, an amino acid sequence.

Some of the mutated proteins were resistant to tyrosine feedback inhibition, and as a result, in one embodiment, may find use in applications for the production of tyrosine.

In one embodiment, the term "resistant" describes a diminished or absent response to a given compound. For example, and in one embodiment, resistance to tyrosine feedback inhibition refers to an absence or diminished effect of tyrosine presence in affecting continued tyrosine production. In one embodiment, such resistance may be reflected as a percent production over wild-type conditions, for example, mutated strain production versus wild-type. The increase in tyrosine production may increase up to 10-fold, in mutated versus wild-type strains, when in the presence of tyrosine.

In one embodiment, the term "feedback inhibition" describes the process of an end product of a particular metabolic reaction inhibiting an allosteric enzyme involved in that reaction, decreasing the effectiveness of the enzyme in further production of the end products.

In one embodiment, tyrosine may be present in nanomolar of micromolar concentrations, which are sufficient to provide some feedback inhibition for further tyrosine production in wild type cells, yet the mutants of this invention will not be inhibited for production, or in another embodiment, the mutants will be somewhat inhibited, yet produce greater amounts of tyrosine, in comparison to wildtype. In one embodiment, the mutants produce enhanced tyrosine, in the presence of tyrosine, at a concentration which ranges from 5 μM-100 μM, or more.

Figure 2:
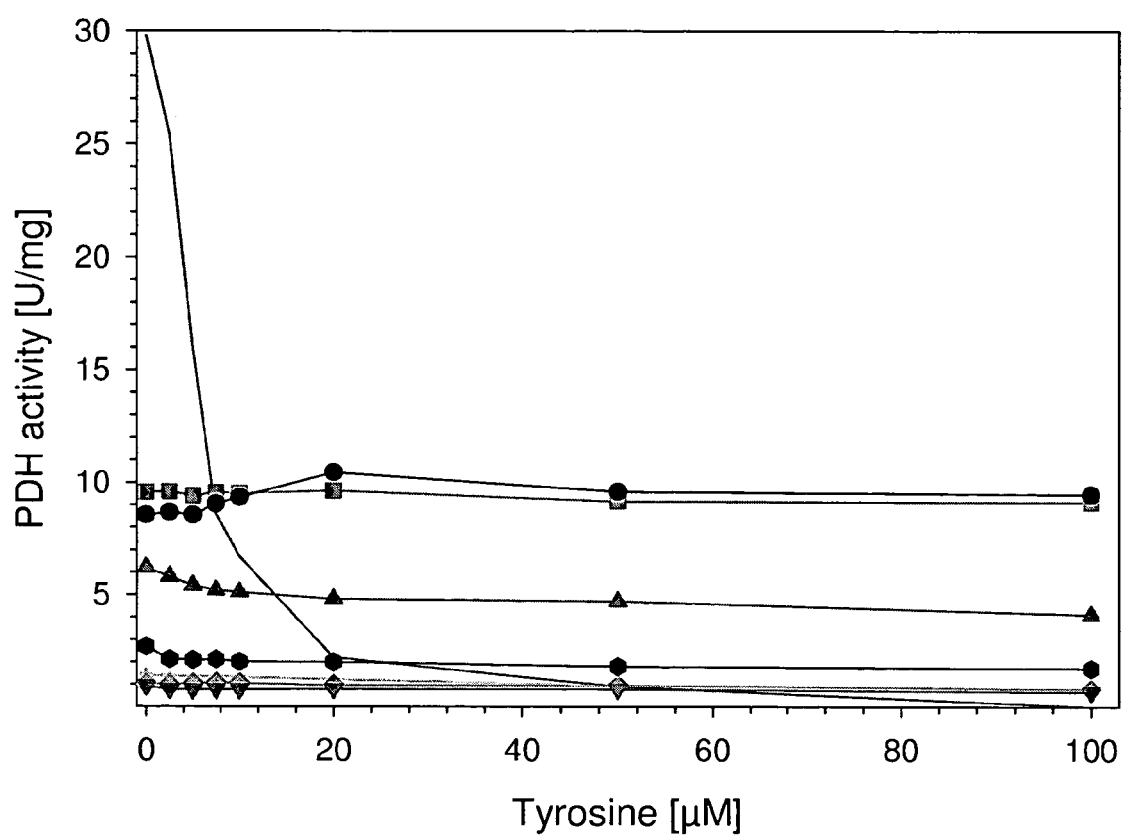
FIG. 2 demonstrates experimental results showing the effect of increasing tyrosine concentrations on prephenate dehydrogenase (PDH) activities of purified TyrA$^{WT}$ and TyrA$^{fbr}$ mutant proteins. The specific PDH activities of eight purified TyrA proteins were measured: −, TyrA$^{WT}$; +, TyrA$^{fb-5}$; ■, TyrA$^{fbr-7}$; ▲, TyrA$^{fbr-10}$; ◆, TyrA$^{fbr-13}$; ▼, TyrA$^{fbr-15}$; ●, TyrA$^{fbr-18}$; ●, TyrA$^{fbr-20}$.

Exemplified herein are various mutations introduced in the CM/PDH protein (some as outlined in FIG. 3), which were diminished in their sensitivity to feedback inhibition by tyrosine (FIG. 2 and Table 1).

The mutants/mutations of this invention are in the tyrA gene, the gene that encodes the CM/PDH protein. In one embodiment, the mutants/mutations of this invention are generated by mutated by any means known in the art, such as, for example, chemical mutagenesis, or via the use of error-prone PCR, as known in the art, and exemplified herein.

As exemplified herein, error-prone PCR was carried out in the presence of 2 and 20 µM 8-oxo-2'-deoxyguanosine (8-oxo-dGTP) and 6-(2-deoxy-β-D-ribofuranosyl)-3,4-dihydro-8H-pyrimido-[4,5-c][1,2]oxazin-7-one (dPTP), as described in Zaccolo, M. et al. 1996 (J. Mol. Biol. 255: 589-603). Mutants may be selected, in some embodiments, on minimal medium supplemented with an amount of tyrosine, which may range, in one embodiment, from 0.5 mM-100 mM. In one embodiment, the selection is with 2 mM m-flouro-D,L-tyrosine.

In another embodiment, the methods of inducing random mutations using PCR are known in the art and, are described, for example, in Dieffenbach (ed) and Dveksler (ed) (In: PCR Primer: A Laboratory Manual, Cold Spring Harbour Laboratories, NY, 1995). In another embodiment, commercially available kits for use in mutagenic PCR are utilized, such as, for example, the Diversify PCR Random Mutagenesis Kit (Clontech) or the GeneMorph Random Mutagenesis Kit (Stratagene).

In another embodiment, site-directed mutagenesis may be used, including the Kunkel, SOE, and Stratagene Quick-change methods. Site-directed methods may be used in one embodiment to delete a portion of the gene or to insert mutations to particular nucleotides that are of specific interest, the latter type of mutation referred to as a point mutation.

In one embodiment, PCR reactions are performed in the presence of at least about 200 mM manganese or a salt thereof. Such concentrations of manganese ion or a manganese salt induce from about 2 mutations per 1000 base pairs (bp) to about 10 mutations every 1000 bp of amplified nucleic acid (Leung et al Technique 1, II-15, 1989).

In another embodiment, PCR reactions are performed in the presence of an elevated or increased or high concentration of dGTP, for example, between about 150 mM and about 200 mM. Such high concentrations of dGTP result in the misincorporation of nucleotides into PCR products at a rate of between about 1 nucleotide and about 3 nucleotides every 1000 bp of amplified nucleic acid (Shahani et al BioTechniques 23, 304-306, 1997).

In another embodiment, the nucleic acid is mutated by insertion into a host cell that is capable of mutating the nucleic acid, producing, in another embodiment, the cells of this invention. Such host cells are deficient in one or more enzymes, such as, for example, one or more recombination or DNA repair enzymes, thereby enhancing the rate of mutation to a rate that is rate approximately 5,000 to 10,000 times higher than for non-mutant cells.

In one embodiment, strains useful for the mutation of nucleic acids carry alleles that modify or inactivate components of the mismatch repair pathway. Examples of such alleles include muff, mutM, mutD, muff, mutA, mutC or mutS. Bacterial cells that carry alleles that modify or inactivate components of the mismatch repair pathway are known in the art, such as, for example the XLlRed, XL-mutS and XL-mutS-Kad bacterial cells (Stratagene).

In another embodiment, the nucleic acid fragments may be cloned into a nucleic acid vector that is preferentially replicated in a bacterial cell by the repair polymerase, Pol I. A Pol I variant strain which induces a high level of mutations in the introduced nucleic acid vector, may be used, in one embodiment, adapting the method described by Fabret et al (In: Nucl Acid Res, 28, 1-5 2000), which is incorporated herein by reference.

In another embodiment, mutagenesis may be accomplished using transposons. In one embodiment, the mariner transposon may be used. Mariner transposition occurs efficiently in vitro, does not require cellular cofactors and shows very little insertion site specificity, requiring only the dinucleotide TA in the target sequence (and even this minor site specificity can be easily altered using different in vitro reaction conditions). In another embodiment, the Tn7 transposon may be used.

Transposons occur naturally as DNA sequences coding for an enzyme, transposase, which recognizes and cuts the DNA at sites flanking the gene for the transposase. The recognition sites, or binding sites for the transposase, are referred to as inverted repeat sequence. As such, transposable elements, when activated, produce an enzyme, which promotes the excision of itself from one location in DNA and the insertion of the excised DNA at another site. In some embodiments, the transposon selected will exhibit site-specific insertion at so-called "hot spots."

In another embodiment, the transposon may be Tn551, Minos, Hermes or piggyback. In another embodiment, the transposon may be AT-2 (tyl based transposon, Perkin Elmer; Devine et al. (1997) Genome Res. 7:551-563), GPS-1 (New England Biolabs), GPS-2 (New England Biolabs), EZ::tn (Tn5 based transposon, Epicenter Technologies), SIF (Tn7 based transposon, Biery et al. (2000) Nucl Acid Res 28:1067-1077), or Mu (Finnzymes, Haapa et al. (1999) Nucl Acid Res 13:2777-2784). It is to be understood that any transposon may be used in the methods of this invention.

The transposons will be employed, in one embodiment, with their natural cognate transposases, or in another embodiment, with the use of modified and/or improved transposases.

In another embodiment, the transposon may comprise a nucleic acid sequence encoding a heterologous polypeptide. This sequence may be integrated, together with the transposon, into the genome of the cell, upon transposon integration. In one embodiment, the heterologous polypeptide may be excised, together with the transposon, when the latter excises on remobilisation. In one embodiment, the heterologous polypeptide is a detectable marker, such as, for example, the green fluorescent protein (GFP), or mutants, homologues thereof.

In one embodiment, this invention provides an isolated nucleic acid comprising a nucleotide sequence sharing homology, as described herein, with the sequence as set forth in SEQ ID Nos: 22-42, wherein the nucleic acid encodes a polypeptide involved in tyrosine biosynthesis.

In one embodiment, the nucleic acids of this invention encode for a mutated version of TyrA. In one embodiment, the encoded mutant will have a substitution of a valine with an isoleucine, a glutamine with an arginine, a phenylalanine with a leucine, or a combination thereof, in the encoded protein. In one embodiment, the mutations will be in sequences which encode for the specific amino acids at position 102, 124, 148, 157, 160, 179, 180, 190, 263, 273, 290, 324, 345, 354, 355, 357, or a combination thereof, in the encoded protein. In another embodiment, the sequence encodes a mutated protein comprising a substitution of a valine with an isoleucine at position 102, a valine with an isoleucine at position 148, a glutamine with an arginine at position 124, a glutamine with an arginine at position 157, a glutamine with an arginine at position 273, a glycine with an aspartic acid at 160, an asparagine with an aspartic acid at position 179, a glycine with an arginine at position 180, an aspartic acid with a glycine at position 190, a tyrosine with a histidine at position 263, a tyrosine with a cysteine at position 263, an alanine with a threonine at position 290, a phenylalanine with a leucine at position 324, a phenylalanine with a leucine at position 357, a lysine with an asparagine at position 345, an alanine with a valine at position 354, a glutamine with a arginine at position 355, or a combination thereof. In another embodiment, the sequence encodes a protein, which comprises an amino acid sequence corresponding to or homologous to SEQ ID Nos: 2-21.

In one embodiment, A nucleic acid molecule of this invention, comprises RNA or DNA that is single- or double-stranded. In another embodiment, the nucleic acid may contain synthetic, non-natural or altered nucleotide bases. A nucleic acid of this invention may comprise a fragment in the form of a polymer of DNA, or may be comprised of one or more segments of cDNA, genomic DNA or synthetic DNA.

In another embodiment, nucleic acids of, and used in this invention comprise analogs of RNA or, in another embodiment, DNA which may be single or double stranded. In one embodiment, the nucleic acids may be in sense or antisense orientation. The nucleic acids of and for use in this invention may include oligonucleotides composed of naturally occurring nucleobases, sugars and covalent internucleoside (backbone) linkages as well as oligonucleotides having non-naturally-occurring portions, which function similarly. Such modified or substituted oligonucleotides are well known in the art, and may impart desirable properties such as, for example, enhanced cellular uptake, enhanced affinity for a nucleic acid target, lipophilicity, solubility, binding affinity to complementary sequences, increased stability in the presence of nucleases or others.

The nucleic acids may be chemically synthesized by methods known in the art, such as, for example in Caruthers (1985) (Science 230:281-285). DNA can also be synthesized by preparing overlapping double-stranded oligonucleotides, filling in the gaps, and ligating the ends together (see, generally, Sambrook et al. (*Molecular Cloning A Laboratory Manual, 2nd Edition*, Vol. 1-3, Cold Spring Harbor Laboratory, Cold Spring Harbor, N.Y., USA, 1989) and Glover et al. (1995) (Cell 81: 95-105). DNA expressing functional homologues of the protein can be prepared from wild-type DNA by site-directed mutagenesis (see, for example, Zoller & Smith (1982) (Nucleic Acids Res. 10(20):6487-500); Zoller & Smith (1983) (Methods Enzymol.; 100:468-500.); and Zoller & Smith (1984) (DNA 3(6):479-88.); McPherson (1991) (*Directed Mutagenesis: A Practical Approach*. Oxford University Press, NY). The DNA obtained can be amplified by methods known in the art. One method may be, in one embodiment, via the use of the polymerase chain reaction (PCR) as described in Saiki et al. (1988) (Science 239:487-491), Mullis et al., U.S. Pat. No. 4,683,195, and Sambrook et al. (1989).

In another embodiment, this invention provides a vector comprising a nucleic acid of this invention, or in another embodiment, a cell comprising a vector of this invention.

In one embodiment, the term "vector" in the present invention, may refer to a nucleic acid construct which further includes an origin of replication, and may be a shuttle vector, which can propagate both in prokaryotic, and in eukaryotic cells, or the vector may be constructed to facilitate its integration within the genome of an organism of choice. The vector, in other embodiments may be, for example, a plasmid, a bacmid, a phagemid, a cosmid, a phage, a virus or an artificial chromosome.

In one embodiment, the vector comprises a sequence of interest and a promoter sequence operatively linked thereto, wherein the promoter may regulate expression.

In another embodiment, the vector contemplated by this invention further comprises an insertion of a heterologous nucleic acid sequence encoding a marker polypeptide. The marker polypeptide may comprise, for example, green fluorescent protein (GFP), DS-Red (red fluorescent protein), secreted alkaline phosphatase (SEAP), beta-galactosidase, luciferase, or any number of other reporter proteins known to one skilled in the art.

In another embodiment, the vectors of this invention which comprise the cassette for expression of the mutated TyrA, may be low-copy or high-copy plasmids, as will be appreciated by one skilled in the art.

In another embodiment, this invention provides an isolated polypeptide with an amino acid sequence homologous to, or corresponding to that of SEQ ID Nos: 2-21.

Cells of this invention may be engineered to comprise mutated DNA, thereby producing the mutated protein. The mutated DNA may be introduced into the cells, by methods well known in the art, whereby either the DNA is directly introduced to the cell, or the DNA is cloned into an expression vector and contacted with a cell to form the cells of this invention.

Incorporation of desired nucleic acid sequences within cells can be accomplished through a number of methods well known in the art. Nucleic acid constructs can be utilized to stably or transiently transfect or transduce the cells.

There are a number of techniques known in the art for introducing vectors into cells of the present invention, such as, but not limited to: direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation or liposome-mediated transfection, (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). Bombardment with nucleic acid coated particles is also envisaged. It is to be understood that any of these methods may be utilized for introduction of the desired sequences into cells, for production of the cells of this invention, and for effecting the methods of this invention, and are to be considered as part of this invention.

Verification of the desired tyrA mutations is readily conducted by methods well known to one skilled in the art. Mutations may be verified via direct DNA sequencing, in one embodiment, or in another embodiment, by southern blot analysis, PCR, and others.

In one embodiment, the nucleic acids of verified mutants are subcloned into a vector, and the mutants are then purified, for example, as described herein, where sequences were subcloned in vector pET-30 Xa/LIC, which included an N-terminal His$_6$-tag for one-step purification.

In one embodiment, the purified products may be concentrated by means well known in the art, including, for example, via dialysis, and protein concentrations estimated by means well known in the art. In one embodiment, protein concentration may be a reflection of the encoded enzyme activity, which may be determined spectrophotometrically, by measuring absorbance at 340 nm, as a function of NADH formation in a reaction mixture containing the enzyme and the starting product prephanate (FIG. 2).

In another embodiment, mutant genes are verified by NADH independent assay for PDH activity, which enables the detection of the formation of a borate complex of 4-hydroxyphenylpyruvate, which has a strong absorption at 330 nm (Dayan and Sprinson (1970) Methods Enzymol. 17: 562-563).

In one embodiment, the genetically engineered cell is a bacterium. In another embodiment, the cell is a yeast cell. In another embodiment, the cell is a plant cell.

In one embodiment, the genetically engineered cell is a bacterium belonging to the *Acinetobacter, Aquifex, Bacillus, Bacteroides, Bordetella, Brevibacterium, Campylobacter, Corynebacterium, Erwinia, Escherichia, Haemophilus, Helicobacter, Idiomarina, Listeria, Pantoea, Photorhabdus, Pseudomonas, Salmonella, Shigella, Staphylococcus, Streptomyces, Synechococcus*, or *Yersinia* genus.

In another embodiment, the genetically engineered cell is a micro-organism with a sequenced genome such as *Actinobacillus pleuropneumoniae, Aeropyrum pernix, Agrobacterium tumeficians, Anopheles gambiae, Aquifex aeolicus, Arabidopsis thaliana, Archeglobus fulgidis, Bacillus anthracis, bacillus cereus, Bacccius halodurans, Bacillus subtilis, Bacteroides thetaiotaomicron, Bdellovibrio bacteriovorus, Bifidobacterium longum, Bordetella bronchiseptica, Bordetella pertussis, Borrelia burgdorferi, Bradyrhizobium japonicum, Brucella melitensis, Brucella suis, Bruchnera aphidicola, Brugia malayi, Caenorhabditis elegans, Campylobacter jejuni, Candidatus blochmanniafloridanus, Caulobacter crescentus, Chlamydia muridarum, Chlamydia trachomatis, Chlamydophilia caviae, Chlamydia pneumoniae, Chlorobium tepidum, Chromobacterium violaceum, Clostridium acetobutylicum, Clostridium perfringens, Clostridium tetani, Corynebacterium diphtheriae, Corynebacterium efficiens, Corynebacterium glutamicum, Coxiella burnetii, Danio rerio, Dechloromonas aromatica, Deinococcus radiodurans, Drosophila melanogaster, Eimeria tenella, Eimeria acervulina, Entamoeba histolytica, Enterococcus faecalis, Escherichia coli, Fusobacterium nucleatum, Geobacter su6rurreducens, Gloeobacter violaceus, Haemophilus ducreyi, Haemophilus influenzae, Halobacterium, Helicobacter hepaticus, Helicobacter pylori, Lactobacillus johnsonii, Lactobacillus plantarum, Lactococcus lactis, Leptospira interrogans serovar lai, Listeria innocua, Listeria monocytogenes, Mesorhizobium loti, Methanobacter thermoautotrophicus, Methanocaldocossus jannaschii, Methanococcoides burtonii, Methanopyrus kandleri, Methanosarcina acetivorans, Methanosareina mazei Goel, Mycobacterium avium, Mycobacterium bovis, Mycobacterium leprae, Mycobacterium tuberculosis, Mycoplasma gallisepticum* strain R, *Mycoplasma genitalium, Mycoplasma penetrans, Mycoplasma pneumoniae, Mycoplasma pulmonis, Nanoarchaeum equitans, Neisseria meningitidis, Nitrosomonas europaea, Nostoc, Oceanobacillus iheyensis, Onion yellows phytoplasma, Oryzias latipes, Oryza sativa, Pasteurella multocida, Photorhabdus luminescens, Pirellula, Plasmodium falciparum, Plasmodium vivax, Plasmodium yoelii, Porphyromonas gingivalis, Prochlorococcus marinus, Pseudomonas aeruginosa, Pseudomonas putida, Pseudomonas syringae, Pyrobaculum aerophilum, Pyrococcus abyssi, Pyrococcus furiosus, Pyrococcus horikoshii, Ralstonia solanacearum, Rhodopseudomonas palustris, Rickettsia conorii, Rickettsia prowazekii, Rickettsii rickettsii, Saccharomyces cerevisiae, Salmonella enterica, Salmonella typhimurium, Sarcocystis cruzi, Schistosoma mansoni, Schizosaccharomyces pombe, Shewanella oneidensis, Shigella flexneri, Sinorhizobium meliloti, Staphylococcus aureus, Staphylococcus epidermidis, Streptococcus agalactiae, Streptococcus agalactiae, Streptococcus mutans, Streptococcus pneumoniae, Streptococcus pyogenes, Streptomyces avermitilis, Streptomyces coelicolor, Suffiblobus tokodaii, Synechocystis* sp., *Takifugu rubripes, Tetraodon fluviatilis, Theileria parva, Thermoanaerobacter tengcongensis, Thernzoplasma acidophilum, Thermoplasma voleanium, Thermosynechococcus elongatus, Aermotoga maritima, Toxoplasma gondii, Treponema denticola, Treponema pallidum, Tropheryma whipplei, Tryponosoma brucei, Trypanosoma cruzi, Ureaplasma urealyticum, Vibrio cholerae, Vibro parahaemolyticus, Pbro vulnificus, Wigglesworthia brevipalpis, Wolbachia endosymbiont* of *Drosophilia melanogaster, W01inella succinogenes, Xanthomonas axonopodis* pv. *Citri, Xanthomonas campestris* pv. *Campestris, Xylella fastidiosa*, or *Yersinia pestis*.

In another embodiment, the genetically engineered cell is a yeast cell belonging to the *Saccharomyces* or *Schizosaccharomyces* genus.

In another embodiment, the bacterium engineered to express a CM/PDH protein in which there is a mutation or mutations in at least one amino acid at position 95-370 of SEQ ID No: 1 belongs to the *Acinetobacter, Aquifex, Bacillus, Bacteroides, Bordetella, Brevibacterium, Campylobacter, Corynebacterium, Erwinia, Escherichia, Haemophilus, Helicobacter, Idiomarina, Listeria, Pantoea, Photorhabdus, Pseudomonas, Salmonella, Shigella, Staphylococcus, Streptomyces, Synechococcus*, or *Yersinia* genus.

In another embodiment, according to this aspect of the invention, the cell belongs to the *Saccharomyces* or *Schizosaccharomyces* genus.

In another embodiment, the genetically engineered cell is a plant cell. According to this aspect of the invention, and in one embodiment, the cells, nucleic acids and methods of this invention may be useful in the preparation of tyrosine enriched crops, or food products.

In another embodiment, the genetically engineered cell further comprises the enzymes involved in tyrosine synthesis, including DAHP (a.k.a DHAP) (3-deoxy-D-arabino-hepturosonate-7-phosphate) synthase, DHQ (dehydroquinate) synthase, DHQ dehydratase, shikimate dehydrogenase, shikimate kinase, EPSP (5-enolpyruvylshikimate-3-phosphate) synthase, chorismate synthase, CM (chorismate mutase), PDH (prephenate dehydratase), tyrosine amino transferase, or a combination thereof.

In one embodiment, this invention provides a method for producing tyrosine, the method comprising engineering a cell to express a CM/PDH protein in which there is a mutation or mutations in at least one amino acid at position 95-370 of SEQ ID No: 1, wherein the cell comprises genes involved in the tyrosine biosynthetic pathway. In one embodiment, the method entails culturing the cells under conditions and for a period of time in which tyrosine can be produced. In one embodiment, the conditions may comprise increased tyrosine concentrations within or surrounding the cell, and tyrosine production is, in one embodiment, unaltered, or in another embodiment, minimally diminished, or in another embodiment, enhanced. In one embodiment, the method may also comprise isolated tyrosine from the culture.

In another embodiment, the methods of this invention result in an increased production of tyrosine by 0.25-10-fold when in the presence of tyrosine, as compared to wildtype cells. In one embodiment, the increase in production will vary as a function of time and culture conditions.

In one embodiment, methods may comprise use of cells which are engineered to over-express a gene encoding tyrosine amino transferase. In one embodiment, cells comprising the vectors, nucleic acids or mutated TyrA of this invention engineered to overexpress a gene encoding tyrosine amino transferase are also to be considered as part of this invention. In another embodiment, this invention provides for vectors comprising expression cassettes encoding the mutated tyrA, and further comprising a gene encoding tyrosine amino transferase, the latter which may be incorporated in single or in multi-copy, as will be appreciated by one skilled in the art. In another embodiment, promoters driving the expression of the respective genes may be chosen to optimize tyrosine production, as will be appreciated by one skilled in the art.

Conditions for tyrosine production may be optimized, as will be appreciated by one skilled in the art, and may include provision of varied carbon source, or in another embodiment, nitrogen source, etc., to the cells and determining optimal tyrosine production, as will be appreciated by one skilled in the art. Similarly, the environmental conditions may be varied, including temperature, or in another embodiment, $CO_2$ or oxygen content, or in another embodiment, atmospheric pressure, or others, as will be appreciated by one skilled in the art.

In another embodiment, this invention provides for the cells, nucleic acids, and/or proteins of this invention for the production of tyrosine-enriched food, food additives, drinks or dietary supplements.

In one embodiment, the tyrosine-enriched food produced is a yogurt, a drink, a shake, an ice cream product, a fruit, or a vegetable.

In another embodiment, the tyrosine-enriched food produced is a candy, chocolate, confection, filled cracker, filled extruded snack, enrobed extruded snack, bar, filled bar, chocolate-covered bar, cracker, spread, cookie, snack crisp, brownie, muffin, potato crisp, sorbet, powder or powder mixture, liquid, pill, capsule, tablet, chewing tablet, gel-cap, effervescent, syrup, lozenge, or spray.

Any of the proposed compositions of this invention may further comprise other active ingredients, which include but are not limited to analgesics, anti-psychotic, anti-anxiolitics, etc., or other compounds which may be useful in treating the conditions described in the context of the invention. In another embodiment, such compositions, in particular compositions for use as food products or additives, may further comprise L-tryptophan, L-dopa, *Arsenicum album, Aurum metallicum, Calcarea carbonica, Causticum, Cimicifuga, Ignatia amara, Kali phosphoricum, Natrum carbonicum, Natrum muriaticum, Pulsatilla, Sepia, Staphysagria, Asparagus cochinchinensis, Ophiopogon japonicus, Salvia miltiorrhiza, Angelica aeutiloba kitagawa, Rehmannia glutinosa Liboschitz, Poria cocos* wolf, *Schizandra chinensis, Platycodon grandiflorum, Polygala tenuifolia, Zizyphus jujuba, Biota orientalis, Pueraria pseudo-hirsuta, Panax ginseng, Codonopsis pilosula, Scrophularia ningpoensis, Glycyrrhiza uralensis, Panax pseudo-ginseng, Ganoderma japonicum, Coptis chinensis, Chrysanthemum morifolium, Phellodendron amurense,* Red ginseng Amber, *Chamomilla, Coffea cruda, Gratiola officinalis, Nux vomica, Thuja occidentalis*, and St. John's Wort.

It is to be understood that any embodiment described herein, as applicable to any and all methods of this invention, is to be considered as part of this invention.

The following are meant to provide materials, methods, and examples for illustrative purposes as a means of practicing/executing the present invention, and are not intended to be limiting.

EXAMPLES

Materials and Methods

Bacterial Strains and Cultivation Conditions

*Escherichia coli* K12 (MG1655), *E. coli* DH5α (Invitrogen) and *E. coli* BL21 (DE3) (Novagen) were used in this study. Cultivations were done at 37° C. in Luria Bertani (LB) or MOPS-buffered minimal medium (Neidhardt, F. C., et al., 1974, *J. Bacteriol.* 119: 736-747). For maintenance of plasmids, 20 µg/ml kanamycin was added.

Isolation, Manipulation and Transfer of DNA

Plasmid DNA was isolated using the Qiaprep Spin Miniprep Kit (Qiagen). Chromosomal DNA from *E. coli* K12 was prepared by using the Wizard Genomic DNA Purification Kit (Promega). Agarose gel purification of DNA fragments was done with the Geneclean Spin Kit (Q-Biogene). Restriction enzymes, ligases and other DNA-manipulating enzymes were used according to the manufacturer's manual. Plasmid DNA was transferred to chemically competent cells of *E. coli* DH5α (Invitrogen) and *E. coli* BL21 (DE3) (Novagen), respectively.

Amplification and Cloning of tyrA$^{WT}$

The wild-type tyrA gene was amplified by PCR from chromosomal DNA of *E. coli* K12 using the following primers: 5'-ccg gta cca tgg ttg ctg aat tga ccg cat tac-3' (tyrA_fw_KpnI; SEQ ID No: 43) and 5'-cca cgc gtt tat tac tgg cga ttg tca ttc gcc-3' (tyrA_rev_MluI; SEQ ID No: 44). After gel purification and digestion with KpnI and MluI, tyrA was cloned into pZE21-MCS1 (Lutz, R. and H. Bujard. 1997. Nucleic Acid Res. 25: 1203-1211) via the respective restriction sites, resulting in plasmid pZE21::tyrA$^{WT}$.

Error-prone PCR and Selection of Feedback Inhibition Resistant tyrA Mutants

Nucleotide analogue mutagenesis was carried out in the presence of 2 and 20 µM 8-oxo-2'-deoxyguanosine (8-oxo-dGTP) and 6-(2-deoxy-β-D-ribofuranosyl)-3,4-dihydro-8H-pyrimido-[4,5-c][1,2]oxazin-7-one (dPTP) (Zaccolo, M., D. et al. 1996, J. Mol. Biol. 255: 589-603). Using the plasmid pZE21::tyrA$^{WT}$ as template, 10, 20 and 30 amplification cycles with the primers mentioned above were performed. The 1.1 kbp PCR products were gel-purified, and the mutated tyrA genes were amplified in a second PCR reaction under regular conditions. Subsequently, the gel-purified DNA fragments were pooled, digested with KpnI and MluI, ligated into pZE21-MCS1, and transformed to highly competent *E. coli* DH5α cells (Invitrogen). Putative tyrA$^{fbr}$ mutants were selected on minimal medium agar plates with 20 µg/ml kanamycin and 2 mM m-flouro-D,L-tyrosine.

Subcloning of tyrA and DNA Sequencing

Putative tyrA$^{fbr}$ genes were amplified by PCR using the following primers: 5'-ggt att gag ggt cgc atg gtt gct gaa ttg acc gca tta c-3' (tyrA_LIC_fw; SEQ ID No: 45) and 5'-aga gga gag tta gag cct tat tac tgg cga ttg tca ttc gcc-3' (tyrA_LIC_rv; SEQ ID No: 46). After gel purification, the PCR products were subcloned into pET-30 Xa/LIC (Novagen) by using ligation-independent cloning (LIC, Novagen), and transformed *E. coli* DH5α (Invitrogen). The resulting plasmids, pET30::tyrA$^{fbr}$, were analyzed by DNA sequencing with the following primers: 5'-TAA TAC GAC TCA CTA TAG GG-3' (T7_prom; SEQ ID No: 47), 5'-GCT AGT TAT TGC TCA GCG G-3' (T7_term; SEQ ID No: 48), 5'-act gcg tcc ggt ggt tat cg-3' (tyrA_291fw; SEQ ID No: 49), and 5'-ggc gaa gag agc gcc aga ag-3' (tyrA_913rv; SEQ ID No: 50).

Expression and Purification of TyrA

For high expression levels of the tyrA$^{fbr}$ genes, the respective pET30::tyrA$^{fbr}$ plasmids were transformed to *E. coli* BL21 (DE3) competent cells (Novagen). The cells were cultivated in LB medium plus 20 μg/ml kanamycin and 1 mM isopropyl-β-D-thiogalactoside (IPTG). After reaching an $OD_{600}$ of ~1, the cells were collected by centrifugation, resuspended in binding buffer (20 mM Tris/HCl, 0.5 M NaCl, 5 mM imidazole, pH 7.9), and disrupted by sonication with a Branson Sonifier 450. The cell extract was centrifugated at 10,000×g for 15 min, and the supernatant was filtered through a 0.45 μm syringe filter (PALL Gelman Laboratory). The native $His_6$-tagged TyrA protein was purified by pre-charged His-Bind column chromatography according to the manufacturer's protocol (Novagen). The eluted protein solution was desalted by Econo-Paco®10DG columns (Biorad) and concentrated by Centriprep®YM10 centrifugal ultrafiltration devices (Millipore). Expression and purification steps were controlled by SDS-PAGE (Laemmli, U. K. 1970. Nature 227: 680-685). Protein concentrations were estimated according to Bradford (Bradford, M. M. 1976. Anal. Biochem. 72: 248-254.).

Prephenate Dehydrogenase (PDH) Activity Measurement in Crude Cell Extracts

Cells of *E. coli* DH5α harboring different pZE21::tyrA$^{fbr}$ derivatives and pZE21::tyrA$^{WT}$, respectively, were cultivated in 100 ml LB medium plus 20 μg/ml kanamycin for 8 h. The cells were harvested, washed with 50 mM Tris/HCl buffer, pH 8.0, and resuspended in 1.5 ml buffer. After sonication, the disrupted cells were centrifuged at 10,000×g for 10 min, and the supernatant containing crude cell extract was collected. This NADH-independent PDH assay is based on the formation of the borate complex of 4-hydroxyphenylpyruvate, which has a strong absorption at 330 nm (Dayan, J., and D. B. Sprinson. 1970. Methods Enzymol. 17: 562-563). 10 μl of crude extract were added to 490 μl of 2 mM $NAD^+$ and 2 mM prephenate in buffer (50 mM Tris, 1 mM EDTA, 1 mM dithioerythritol, pH 8.0) and incubated at 37° C. for 30 min. The reaction was stopped by addition of 100 μl of 15% trichloroacetic acid, the samples were chilled on ice for 5 min and the precipitated proteins were separated by centrifugation for 5 min at 12,000×g. Each 200 μl of the supernatant were added to, (i) 1 ml of 1 M boric acid in 2 M sodium arsenate, pH 6.5 (sample) and, (ii) 1 ml of 2 M sodium arsenate, pH 6.5 (blank). After incubation for 10 min at room temperature, the absorbance was measured at 330 nm.

PDH Activity Measurement with Purified TyrA Proteins

PDH activities of purified TyrA proteins were determined spectrophotometrically according to NADH formation (Davidson, B. E., and G. S. Hudson. 1987. Methods Enzymol. 142: 440-450). 1 ml of 0.2 mM prephenate, 2 mM $NAD^+$, 0.1 mg/ml bovine serum albumin and 10 mM 2-mercaptoethanol in 50 mM Tris/HCl buffer with 1 mM EDTA, pH 8.0, was preheated for 5 min at 37° C. The reaction was started by addition of approximately 0.1 μg of enzyme which corresponded to 5-20 μl of enzyme solution, and the absorbance at 340 nm was followed for 2 min.

Chorismate Mutase (CM) Activity with Purified TyrA Proteins

CM activities were determined spectrophotometrically based on the formation of phenylpyruvate by treatment with HCl (Davidson, B. E., and G. S. Hudson. 1987. Methods Enzymol. 142: 440-450). The reaction mixture contained 1 mM chorismate, 0.1 mg/ml bovine serum albumin and 10 mM 2-mercaptoethanol in 50 mM Tris/HCl buffer with 1 mM EDTA, pH 8.0, and 0.4 ml of this solution was preheated for 5 min at 37° C. in a water bath. After addition of 5-20 μl of enzyme solution, the reaction was incubated at 37° C. for 5 min. For the conversion of chorismate to phenylpyruvate, 0.4 ml of 1 M HCl was added and further incubated at 37° C. for 10 min. The samples were alkalized with 1 ml of 2.5 M NaOH, and the absorbance was measured at 320 nm according to a blank sample without enzyme.

Chemicals

Chorismate, prephenate, 4-hydroxyphenylpyruvate and m-flouro-D,L-tyrosine were obtained from Sigma. Other chemicals, biochemicals and enzymes were obtained from VWR International, Novagen, Teknova, Invitrogen, Biorad, New England Biolabs or Sigma.

Example 1

PDH Activity of WT and CM/PDH Mutants in Response to Tyrosine

Mutants of the tyrA gene from *E. coli* K12 were generated by error-prone PCR and cloned into pZE21-MCS1. After transformation into *E. coli* DH5α those strains were selected which were capable of growing in the presence of ≧2 mM m-fluoro-D,L-tyrosine, a tyrosine analogue which inhibits growth of *E. coli* DH5α harboring plasmid pZE21::tyrA$^{WT}$. From 621 obtained tyrA$^{fbr}$ mutants, seven mutants were chosen for detailed analyses. FIG. 1 shows that the tyrA$^{fbr}$ containing plasmids enabled growth of the *E. coli* DH5α host strains in the presence of m-fluoro-D,L-tyrosine, in contrast to the *E. coli* DH5α strain expressing the tyrA$^{WT}$ gene. Growth of *E. coli* DH5α without plasmid was inhibited at concentrations of ≧0.1 mM m-fluoro-D,L-tyrosine, and addition of equimolar amounts of L-tyrosine restored growth.

The effect of tyrosine on the mutated TyrA proteins of twenty different *E. coli* DH5α strains expressing putative tyrA$^{fbr}$ genes was studied by measuring the PDH activities in crude extracts. The PDH activity of *E. coli* DH5α pZE21:: tyrA$^{WT}$ was reduced from 72.4 U/g to 37.6 U/g when 1 mM tyrosine was added to the enzyme assay. In contrast, tyrosine did not affect PDH activities of *E. coli* DH5α pZE21::tyrA$^{fbr}$, which were in the range between 40.7 to 84.6 U/g.

Seven different tyrA$^{fbr}$ and the tyrA$^{WT}$ genes were subcloned into vector pET-30 Xa/LIC, which included an N-terminal $His_6$-tag for one-step purification of the respective fusion proteins. The resulting pET30::tyrA$^{fbr}$ plasmids as well as pET30::tyrA$^{WT}$ were expressed in *E. coli* BL21 (DE3) after induction with 1 mM IPTG. The $His_6$-tagged TyrA proteins were purified to homogeneity and used for NADH-dependent enzyme assays. The specific PDH activity of TyrA$^{WT}$ decreased significantly in the presence of tyrosine. While the specific PDH activity of TyrA$^{WT}$ was 29.8 U/mg in the absence of tyrosine, it dropped to less than 10% of that activity in the presence of 20 μM tyrosine (FIG. 2). In contrast, all TyrA$^{fbr}$ mutants showed lower activities in the absence of tyrosine, but tyrosine concentrations of up to 100 μM did not significantly decrease the PDH activities. While four mutants exhibited less than 10% activity as compared to TyrA$^{WT}$, the mutants TyrA$^{mut-7}$, TyrA$^{mut-10}$ and TyrA$^{mut-20}$ showed 21 to 35% of the wild-type PDH activity. Interestingly, the PDH activity of TyrA$^{mut-20}$ slightly increased with increasing tyrosine concentrations of up to 20 μM (FIG. 2).

Thus, the relationship between the ability of E. Coli to grow in the presence of m-fluoro-D,L-tyrosine and the alleviation of the feedback inhibition by tyrosine was confirmed by the biochemical characterization of seven representatives of tyrA$^{fbr}$ mutants. Although all TyrA$^{fbr}$ showed reduced PDH activities in the absence of tyrosine, addition of tyrosine did not inhibit the enzyme activity as it did in TyrA$^{WT}$ (FIG. 2). Hence, this invention is the first to demonstrate TyrA mutants that are feedback-resistant to tyrosine.

Example 2

CM Activity of Mutant and WT CM/PDH in the Presence of Tyrosine and NAD$^+$

Mutants were generated, selected, and their proteins were isolated as described in Example 1. The CM activities of the purified TyrA proteins were then examined. TyrA$^{mut-7}$ and TyrA$^{mut-20}$ showed slightly higher specific activities, whereas all other mutants exhibited lower CM activities (Table 1). When 100 μM tyrosine and NAD$^+$ were added, all TyrA proteins revealed a 43 to 96% reduction in CM activity, indicating that the effect of tyrosine on the TyrA$^{fbr}$ mutants is comparable with the TyrA$^{WT}$. Thus, the feedback regulation of the tyrA$^{fbr}$ mutants affects only the PDH and not the CM domain of TyrA.

TABLE 1

PDH and CM activities of purified TyrA$^{fbr}$ mutants and TyrA$^{WT}$. The specific enzyme activities of purified TyrA proteins were determined in the presence and absence of 100 μM tyrosine.

|  | PDH activity [U/mg] | | CM activity [U/mg] | |
| --- | --- | --- | --- | --- |
|  | 0 μM Tyrosine | 100 μM Tyrosine | 0 μM Tyrosine | 100 μM Tyrosine* |
| TyrA$^{WT}$ | 29.80 | nd | 1.32 | 1.23 |
| TyrA$^{mut-5}$ | 1.40 | 0.81 | 0.03 | 0.03 |
| TyrA$^{mut-7}$ | 9.56 | 9.12 | 1.84 | 0.79 |
| TyrA$^{mut-10}$ | 6.15 | 4.07 | 0.24 | 0.18 |
| TyrA$^{mut-13}$ | 1.00 | 0.76 | 0.53 | 0.47 |
| TyrA$^{mut-15}$ | 0.93 | 0.66 | 0.52 | 0.37 |
| TyrA$^{mut-18}$ | 2.69 | 1.70 | 1.07 | 0.69 |
| TyrA$^{mut-20}$ | 8.55 | 9.46 | 1.56 | 1.50 | nd not detectable;
*in the presence of 100 μM NAD$^+$.

Example 3

Identification of Mutations Conferring Tyrosine Feedback-Inhibition Resistance

Mutants were generated and selected as described in Example 1. All tyrA mutants were sequenced, and FIG. 3 shows the amino acid sequence alignment of the tyrA$^{fbr}$ mutants with the tyrA$^{WT}$. The mutants revealed one to four amino acid exchanges in the C-terminal PDH domain, whereas none, one or two amino acids were substituted in the N-terminal CM domain. Interestingly, all mutants had one of the following mutated loci in the PDH domain: Y263H, A354V, or F357L.

The DNA sequences of the tyrA$^{fbr}$ genes generated in this study have been analyzed and compared to the tyrA$^{WT}$ gene (FIG. 3). The number of amino acid substitutions varied from two (tyrA$^{mut-20}$) to six (tyrA$^{mut-5}$), whereas TyrA$^{mut-20}$ revealed the highest PDH activity comprising 35% of the TyrA$^{WT}$ activity, and even a slightly increased CM activity (Table 1). Residues 354 to 357 seem to be involved in the inhibitory binding of tyrosine, because A354V and F357L substitutions alleviated feedback inhibition of the PDH domain. Although F357L was the most frequent mutation, Q355R substitutions were also identified in tyrA$^{fbr}$ mutants (data not shown). Those mutants that did not possess amino acid alterations at these residues, revealed either a Y263H or a Y263C substitution (data not shown), strongly indicating that Tyr263 is also involved in the feedback inhibition mechanism. However, there was no obvious relationship between the mutations at these two sites and the corresponding PDH activities, i.e. mutants with either amino acid exchange did not show generally higher or lower PDH activity.

What is claimed is:

1. A cell engineered to express a chorismate mutase/prephenate dehydrogenase (CM/PDH) protein having at least 95% identity to SEQ ID NO: 1, wherein said protein
   a) comprises a mutation in at least one amino acid at positions 95, 96, 180, 190, 324 or 357 of SEQ ID NO: 1; and
   b) is subject to lower or no feedback inhibition by tyrosine.

2. The cell of claim 1, wherein said mutation comprises a substitution of a phenylalanine with a leucine.

3. The cell of claim 1, wherein said mutation is at position: 180, 190, 324, 357, or a combination thereof.

4. The cell of claim 1, wherein said mutation comprises a substitution of: a glycine with an arginine at position 180, an aspartic acid with a glycine at position 190, a phenylalanine with a leucine at position 324, a phenylalanine with a leucine at position 357, or a combination thereof.

5. The cell of claim 1, wherein said cell is a bacterium or a yeast.

6. The cell of claim 5, wherein said bacterium belongs to the *Acinetobacter, Aquifex, Bacillus, Bacteroides, Bordetella, Brevibacterium, Campylobacter, Corynebacterium, Erwinia, Escherichia, Haemophilus, Helicobacter, Idiomarina, Listeria, Pantoea, Photorhabdus, Pseudomonas, Salmonella, Shigella, Staphylococcus, Streptomyces, Synechococcus,* or *Yersinia* genus.

7. The cell of claim 5, wherein said yeast cell belongs to the *Saccharomyces* or *Schizosaccharomyces* genus.

8. An isolated nucleic acid comprising the nucleotide sequence as set forth in SEQ ID NO: 26, wherein said nucleic acid encodes a polypeptide involved in tyrosine biosynthesis.

9. A vector comprising the nucleic acid of claim 8.

10. A cell comprising the vector of claim 9.

11. A cell engineered to express a chorismate mutase/prephenate dehydrogenase (CM/PDH) protein, wherein said protein
   a) has the amino acid sequence as set forth in SEQ ID NO: 5; and
   b) is subject to lower or no feedback inhibition by tyrosine.

* * * * *

SEQUENCE LISTING

<160> NUMBER OF SEQ ID NOS: 50

<210> SEQ ID NO 1
<211> LENGTH: 373
<212> TYPE: PRT
<213> ORGANISM: Escherichia coli

<400> SEQUENCE: 1

Met Val Ala Glu Leu Thr Ala Leu Arg Asp Gln Ile Asp Glu Val Asp
1               5                   10                  15

```
Lys Ala Leu Leu Asn Leu Leu Ala Lys Arg Leu Glu Leu Val Ala Glu
                 20                  25                  30

Val Gly Glu Val Lys Ser Arg Phe Gly Leu Pro Ile Tyr Val Pro Glu
             35                  40                  45

Arg Glu Ala Ser Met Leu Ala Ser Arg Ala Glu Ala Glu Ala Leu
         50                  55                  60

Gly Val Pro Pro Asp Leu Ile Glu Asp Val Leu Arg Arg Val Met Arg
 65                  70                  75                  80

Glu Ser Tyr Ser Ser Glu Asn Asp Lys Gly Phe Lys Thr Leu Cys Pro
                 85                  90                  95

Ser Leu Arg Pro Val Val Ile Val Gly Gly Gly Gln Met Gly Arg
             100                 105                 110

Leu Phe Glu Lys Met Leu Thr Leu Ser Gly Tyr Gln Val Arg Ile Leu
             115                 120                 125

Glu Gln His Asp Trp Asp Arg Ala Ala Asp Ile Val Ala Asp Ala Gly
         130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                 165                 170                 175

Val Lys Asn Gly Pro Leu Gln Ala Met Leu Val Ala His Asp Gly Pro
             180                 185                 190

Val Leu Gly Leu His Pro Met Phe Gly Pro Asp Ser Gly Ser Leu Ala
             195                 200                 205

Lys Gln Val Val Val Trp Cys Asp Gly Arg Lys Pro Glu Ala Tyr Gln
         210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                 245                 250                 255

His Phe Ala Thr Phe Ala Tyr Gly Leu His Leu Ala Glu Glu Asn Val
             260                 265                 270

Gln Leu Glu Gln Leu Leu Ala Leu Ser Ser Pro Ile Tyr Arg Leu Glu
         275                 280                 285

Leu Ala Met Val Gly Arg Leu Phe Ala Gln Asp Pro Gln Leu Tyr Ala
         290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                 325                 330                 335

Gln Ala Phe Ile Asp Ser Phe Arg Lys Val Glu His Trp Phe Gly Asp
             340                 345                 350

Tyr Ala Gln Arg Phe Gln Ser Glu Ser Arg Val Leu Leu Arg Gln Ala
             355                 360                 365

Asn Asp Asn Arg Gln
    370

<210> SEQ ID NO 2
<211> LENGTH: 373
<212> TYPE: PRT
<213> ORGANISM: Escherichia coli

<400> SEQUENCE: 2

Met Val Ala Glu Leu Thr Ala Leu Arg Asp Gln Ile Asp Glu Val Asp
```

```
              1               5              10              15

Lys Ala Leu Leu Asn Leu Leu Ala Lys Arg Leu Gly Leu Val Ala Glu
                         20                  25                  30

Val Gly Glu Val Lys Ser Arg Phe Gly Leu Pro Ile His Val Pro Glu
                     35                  40                  45

Arg Glu Ala Ser Met Leu Ala Ser Arg Ala Glu Ala Glu Ala Leu
                 50                  55                  60

Gly Val Pro Pro Asp Leu Ile Glu Asp Val Leu Arg Arg Val Met Arg
         65                  70                  75                  80

Glu Ser Tyr Ser Ser Glu Asn Asp Lys Gly Phe Lys Thr Leu Cys Pro
                             85                  90                  95

Ser Leu Arg Pro Val Val Ile Val Gly Gly Gly Gln Met Gly Arg
                        100                 105                 110

Leu Phe Glu Lys Met Leu Thr Leu Ser Gly Tyr Gln Val Arg Ile Leu
                    115                 120                 125

Glu Gln His Asp Trp Asp Arg Ala Ala Asp Ile Val Ala Asp Ala Gly
                130                 135                 140

Met Val Ile Val Ser Val Pro Ile His Val Thr Glu Gln Val Ile Gly
        145                 150                 155                 160

Lys Leu Pro Pro Leu Pro Lys Asp Cys Ile Leu Val Asp Leu Ala Ser
                        165                 170                 175

Val Lys Asn Gly Pro Leu Gln Ala Met Leu Val Ala His Asp Gly Pro
                    180                 185                 190

Val Leu Gly Leu His Pro Met Phe Gly Pro Asp Ser Gly Ser Leu Ala
                195                 200                 205

Lys Gln Val Val Val Trp Cys Asp Gly Arg Lys Pro Glu Ala Tyr Gln
                210                 215                 220

Trp Phe Leu Glu Gln Ile Gln Val Trp Gly Ala Arg Leu His Arg Ile
        225                 230                 235                 240

Ser Ala Val Glu His Asp Gln Asn Met Ala Phe Ile Gln Ala Leu Arg
                        245                 250                 255

His Phe Ala Thr Phe Ala His Gly Leu His Leu Ala Glu Glu Asn Val
                    260                 265                 270

Gln Leu Glu Gln Leu Leu Val Leu Ser Ser Pro Ile Tyr Arg Leu Glu
                275                 280                 285

Leu Ala Met Val Gly Arg Leu Phe Ala Gln Asp Pro Gln Leu Tyr Ala
                290                 295                 300

Asp Ile Ile Met Ser Ser Glu Arg Asn Leu Ala Leu Ile Lys Arg Tyr
        305                 310                 315                 320

Tyr Lys Arg Phe Gly Glu Ala Ile Glu Leu Leu Glu Gln Gly Asp Lys
                        325                 330                 335

Gln Ala Phe Ile Asp Ser Phe Arg Lys Val Glu His Trp Phe Gly Asp
                    340                 345                 350

Tyr Ala Gln Arg Phe Gln Ser Glu Ser Arg Val Leu Leu Arg Gln Ala
                355                 360                 365

Asn Asp Asn Arg Gln
                370

<210> SEQ ID NO 3
<211> LENGTH: 373
<212> TYPE: PRT
<213> ORGANISM: Escherichia coli

<400> SEQUENCE: 3
```

-continued

```
Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Gly Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Thr Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asp Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Phe Ser Pro Ile Tyr Arg Leu Glu
        275                 280                 285

Leu Ala Met Val Gly Arg Leu Phe Ala Gln Asp Pro Gln Leu Cys Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
    370
```

<210> SEQ ID NO 4
<211> LENGTH: 373
<212> TYPE: PRT
<213> ORGANISM: Escherichia coli

<400> SEQUENCE: 4

```
Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Glu Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
            165                 170                 175

Val Lys Asn Gly Pro Leu Gln Ala Met Leu Val Ala His Asp Gly Pro
        180                 185                 190

Val Leu Gly Leu His Pro Met Phe Gly Pro Asp Ser Gly Ser Leu Ala
    195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
            245                 250                 255

His Phe Ala Thr Phe Ala Cys Gly Leu His Leu Ala Glu Glu Asn Val
        260                 265                 270

Gln Leu Glu Gln Leu Leu Ala Leu Ser Ser Pro Ile Tyr Arg Leu Glu
    275                 280                 285

Leu Ala Met Val Gly Arg Leu Phe Ala Gln Asp Pro Gln Leu Tyr Ala
290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Gly Lys
            325                 330                 335

Gln Ala Phe Ile Asp Ser Phe Arg Lys Val Glu His Trp Phe Gly Asp
        340                 345                 350

Tyr Ala Gln Arg Phe Gln Ser Glu Ser Arg Val Leu Leu Arg Gln Ala
    355                 360                 365

Asn Asp Asn Arg Gln
    370

<210> SEQ ID NO 5
<211> LENGTH: 373
<212> TYPE: PRT
<213> ORGANISM: Escherichia coli
```

```
<400> SEQUENCE: 5

Met Val Ala Glu Leu Thr Ala Leu Arg Asp Gln Ile Asp Glu Val Asp
 1               5                  10                  15

Lys Ala Leu Leu Asn Leu Leu Ala Lys Arg Leu Glu Leu Val Ala Glu
             20                  25                  30

Val Gly Glu Val Lys Ser Arg Phe Gly Leu Pro Ile Tyr Val Pro Glu
         35                  40                  45

Arg Glu Ala Ser Met Leu Ala Ser Arg Arg Ala Glu Ala Glu Ala Leu
     50                  55                  60

Gly Val Pro Pro Asp Leu Ile Glu Asp Val Leu Arg Arg Val Met Arg
 65                  70                  75                  80

Glu Ser Tyr Ser Ser Glu Asn Asp Lys Gly Phe Lys Thr Leu Cys Pro
                 85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Leu Gln Ser Glu Ser Arg Val Leu Leu Arg Gln Ala
        355                 360                 365

Asn Asp Asn Arg Gln
        370

<210> SEQ ID NO 6
<211> LENGTH: 373
<212> TYPE: PRT
<213> ORGANISM: Escherichia coli
```

<400> SEQUENCE: 6

```
Met Val Ala Glu Leu Thr Ala Leu Arg Asp Gln Ile Asp Glu Val Asp
1               5                   10                  15
Lys Ala Leu Leu Asn Leu Leu Ala Lys Arg Leu Glu Leu Val Ala Glu
            20                  25                  30
Val Gly Glu Val Glu Ser Arg Phe Gly Leu Pro Ile Tyr Val Ser Glu
        35                  40                  45
Arg Glu Ala Ser Met Leu Ala Ser Arg Arg Ala Glu Ala Glu Ala Leu
    50                  55                  60
Gly Val Pro Pro Asp Leu Ile Glu Asp Val Leu Arg Arg Val Met Arg
65                  70                  75                  80
Glu Ser Tyr Ser Ser Glu Asn Asp Lys Gly Phe Lys Thr Leu Cys Pro
                85                  90                  95
Ser Leu Arg Pro Val Val Ile Val Gly Gly Gly Gln Met Gly Arg
            100                 105                 110
Leu Phe Glu Lys Met Leu Thr Leu Ser Gly Tyr Gln Val Arg Ile Leu
        115                 120                 125
Glu Gln His Asp Trp Asp Arg Ala Ala Asp Ile Val Ala Asp Ala Gly
    130                 135                 140
Met Val Ile Val Ser Val Pro Ile His Val Thr Glu Gln Val Ile Gly
145                 150                 155                 160
Lys Leu Pro Pro Leu Pro Lys Asp Cys Ile Leu Val Asp Leu Ala Ser
                165                 170                 175
Val Lys Asn Arg Pro Leu Gln Ala Met Leu Val Ala His Asp Gly Pro
            180                 185                 190
Val Leu Gly Leu His Pro Met Phe Gly Pro Asp Ser Gly Ser Leu Ala
        195                 200                 205
Lys Gln Val Val Val Trp Cys Asp Gly Arg Lys Pro Glu Ala Tyr Gln
    210                 215                 220
Trp Phe Leu Glu Gln Ile Gln Val Trp Gly Ala Arg Leu His Arg Ile
225                 230                 235                 240
Ser Ala Val Glu His Asp Gln Asn Met Ala Phe Ile Gln Ala Leu Arg
                245                 250                 255
His Phe Ala Thr Phe Ala Tyr Gly Leu His Leu Ala Glu Glu Asn Val
            260                 265                 270
Gln Leu Glu Gln Leu Leu Ala Leu Ser Ser Pro Ile Tyr Arg Leu Glu
        275                 280                 285
Leu Ala Met Val Gly Arg Leu Phe Ala Gln Asp Pro Gln Leu Tyr Ala
    290                 295                 300
Asp Ile Ile Met Ser Ser Glu Arg Asn Leu Ala Leu Ile Lys Arg Tyr
305                 310                 315                 320
Tyr Lys Arg Phe Gly Glu Ala Ile Glu Leu Leu Glu Gln Gly Asp Lys
                325                 330                 335
Gln Ala Phe Ile Asp Ser Phe Arg Lys Val Glu His Trp Phe Gly Asp
            340                 345                 350
Tyr Ala Gln Arg Leu Gln Ser Glu Ser Arg Val Leu Leu Arg Gln Ala
        355                 360                 365
Asn Asp Asn Arg Gln
    370

<210> SEQ ID NO 7
<211> LENGTH: 373
<212> TYPE: PRT
```

```
<213> ORGANISM: Escherichia coli
<220> FEATURE:
<221> NAME/KEY: misc_feature
<222> LOCATION: (367)..(367)
<223> OTHER INFORMATION: Xaa can be any naturally occurring amino acid

<400> SEQUENCE: 7
```

| | | | | | | | | | | | | | | |
|---|---|---|---|---|---|---|---|---|---|---|---|---|---|---|
| Met | Val | Ala | Glu | Leu | Thr | Ala | Leu | Arg | Asp | Gln | Ile | Asp | Glu | Val | Asp |
| 1 | | | | 5 | | | | | 10 | | | | | 15 | |
| Lys | Ala | Leu | Leu | Asn | Leu | Leu | Ala | Lys | Arg | Leu | Glu | Leu | Val | Ala | Glu |
| | | | 20 | | | | | 25 | | | | | 30 | | |
| Val | Gly | Glu | Val | Lys | Ser | Arg | Phe | Gly | Leu | Pro | Ile | Tyr | Val | Pro | Glu |
| | 35 | | | | | 40 | | | | | 45 | | | | |
| Arg | Glu | Ala | Ser | Met | Leu | Ala | Ser | Arg | Ala | Glu | Ala | Glu | Ala | Leu |
| 50 | | | | | 55 | | | | | 60 | | | | |
| Gly | Val | Pro | Pro | Asp | Leu | Ile | Glu | Asp | Val | Leu | Arg | Arg | Val | Met | Arg |
| 65 | | | | 70 | | | | | 75 | | | | | 80 | |
| Glu | Ser | Cys | Ser | Ser | Glu | Ser | Asp | Lys | Gly | Phe | Lys | Thr | Leu | Cys | Pro |
| | | | | 85 | | | | | 90 | | | | | 95 | |
| Ser | Leu | Arg | Pro | Val | Val | Ile | Val | Gly | Gly | Gly | Gln | Met | Gly | Arg |
| | | 100 | | | | | 105 | | | | | 110 | | | |
| Leu | Phe | Glu | Lys | Met | Leu | Thr | Leu | Ser | Gly | Tyr | Gln | Val | Arg | Ile | Leu |
| | | 115 | | | | | 120 | | | | | 125 | | | |
| Glu | Gln | His | Asp | Trp | Asp | Arg | Ala | Ala | Asp | Ile | Val | Ala | Asp | Ala | Gly |
| 130 | | | | | 135 | | | | | 140 | | | | | |
| Met | Val | Ile | Val | Ser | Val | Pro | Ile | His | Val | Thr | Glu | Gln | Val | Ile | Gly |
| 145 | | | | | 150 | | | | | 155 | | | | | 160 |
| Lys | Leu | Pro | Pro | Leu | Pro | Lys | Asp | Cys | Ile | Leu | Val | Asp | Leu | Ala | Ser |
| | | | | 165 | | | | | 170 | | | | | 175 | |
| Val | Lys | Asn | Gly | Pro | Leu | Gln | Ala | Met | Leu | Val | Ala | His | Asp | Gly | Pro |
| | | | 180 | | | | | 185 | | | | | 190 | | |
| Val | Leu | Gly | Leu | His | Pro | Met | Phe | Gly | Pro | Asp | Ser | Gly | Ser | Leu | Ala |
| | | 195 | | | | | 200 | | | | | 205 | | | |
| Lys | Gln | Val | Val | Val | Trp | Cys | Asp | Gly | Arg | Lys | Pro | Glu | Ala | Tyr | Gln |
| 210 | | | | | 215 | | | | | 220 | | | | | |
| Trp | Phe | Leu | Glu | Gln | Ile | Gln | Val | Trp | Gly | Ala | Arg | Leu | His | Arg | Ile |
| 225 | | | | | 230 | | | | | 235 | | | | | 240 |
| Ser | Ala | Val | Glu | His | Asp | Gln | Asn | Met | Ala | Phe | Ile | Gln | Ala | Leu | Arg |
| | | | | 245 | | | | | 250 | | | | | 255 | |
| His | Phe | Ala | Ala | Phe | Ala | Tyr | Gly | Leu | His | Leu | Ala | Glu | Glu | Asn | Val |
| | | | 260 | | | | | 265 | | | | | 270 | | |
| Gln | Leu | Glu | Gln | Leu | Leu | Ala | Leu | Ser | Ser | Pro | Ile | Tyr | Pro | Leu | Glu |
| | | 275 | | | | | 280 | | | | | 285 | | | |
| Leu | Ala | Met | Val | Gly | Arg | Leu | Phe | Ala | Gln | Asp | Pro | Gln | Leu | Tyr | Ala |
| | | 290 | | | | | 295 | | | | | 300 | | | |
| Asp | Ile | Ile | Met | Ser | Ser | Glu | Arg | Asn | Leu | Ala | Leu | Ile | Lys | Arg | Tyr |
| 305 | | | | | 310 | | | | | 315 | | | | | 320 |
| Tyr | Lys | Arg | Phe | Gly | Glu | Ala | Ile | Glu | Leu | Gln | Glu | Gln | Gly | Asp | Lys |
| | | | | 325 | | | | | 330 | | | | | 335 | |
| Gln | Ala | Phe | Asn | Asp | Ser | Phe | Pro | Lys | Val | Glu | His | Trp | Phe | Gly | Asp |
| | | | 340 | | | | | 345 | | | | | 350 | | |
| Tyr | Ala | Gln | Arg | Leu | Gln | Ser | Glu | Ser | Arg | Val | Leu | Leu | Arg | Xaa | Ala |
| | | 355 | | | | | 360 | | | | | 365 | | | |
| Asn | Asp | Asn | Arg | Gln |
| | 370 | | | | |

<210> SEQ ID NO 8
<211> LENGTH: 373
<212> TYPE: PRT
<213> ORGANISM: Escherichia coli

<400> SEQUENCE: 8

```
Met Val Ala Glu Leu Thr Ala Leu Arg Asp Arg Ile Asp Glu Val Asp
1               5                   10                  15

Lys Ala Leu Leu Asn Leu Leu Ala Lys Arg Leu Glu Leu Ala Ala Glu
                20                  25                  30

Val Gly Glu Val Lys Ser Arg Phe Gly Leu Pro Ile Tyr Val Pro Glu
            35                  40                  45

Arg Glu Ala Ser Met Leu Ala Ser Arg Arg Ala Glu Ala Glu Ala Leu
        50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
                100                 105                 110

Leu Phe Glu Lys Met Leu Thr Leu Ser Gly Tyr Gln Val Arg Ile Leu
            115                 120                 125

Glu Gln His Asp Trp Asp Arg Ala Ala Asp Ile Val Ala Asp Ala Gly
        130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
                180                 185                 190

Val Leu Gly Leu His Pro Met Phe Gly Pro Asp Ser Gly Ser Leu Ala
            195                 200                 205

Lys Gln Val Val Val Trp Cys Asp Gly Arg Lys Pro Glu Ala Tyr Gln
        210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala His Gly Leu His Leu Ala Glu Glu Asn Val
                260                 265                 270

Gln Leu Glu Gln Leu Leu Ala Leu Ser Ser Pro Ile Tyr Arg Leu Glu
            275                 280                 285

Leu Ala Met Val Gly Arg Leu Phe Ala Gln Asp Pro Gln Leu Tyr Ala
        290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Glu Gln Gly Asp Lys
                325                 330                 335

Gln Ala Phe Ile Asp Ser Phe Arg Lys Val Glu His Trp Phe Gly Asp
                340                 345                 350

Tyr Ala Gln Arg Phe Gln Ser Glu Ser Arg Val Leu Leu Arg Gln Ala
            355                 360                 365

Asn Asp Asn Arg Gln
```

370

<210> SEQ ID NO 9
<211> LENGTH: 373
<212> TYPE: PRT
<213> ORGANISM: Escherichia coli

<400> SEQUENCE: 9

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala His Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
    370

<210> SEQ ID NO 10
<211> LENGTH: 373
<212> TYPE: PRT
<213> ORGANISM: Escherichia coli

<400> SEQUENCE: 10

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Cys Ile
225                 230                 235                 240

Ser Ala Val Glu His Asp Gln Ser Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Arg Leu Leu Ala Leu Ser Ser Leu Ile Tyr Arg Leu Glu
        275                 280                 285

Leu Ala Met Val Gly Arg Leu Phe Ala Arg Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
    370

<210> SEQ ID NO 11
<211> LENGTH: 373
<212> TYPE: PRT
<213> ORGANISM: Escherichia coli

<400> SEQUENCE: 11

Met Val Ala Glu Leu Thr Ala Leu Cys Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Pro Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Ser Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Arg Leu Leu Ala Leu Ser Ser Pro Ile Tyr Arg Leu Glu
        275                 280                 285

Leu Ala Met Val Gly Arg Leu Phe Ala Arg Asp Pro Gln Leu Tyr Ala
    290                 295                 300

Asp Ile Ile Met Leu Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Leu Gln Ser Glu Ser Arg Val Leu Leu Arg Gln Ala

Asn Asp Asn Arg Gln
    370

<210> SEQ ID NO 12
<211> LENGTH: 373
<212> TYPE: PRT
<213> ORGANISM: Escherichia coli

<400> SEQUENCE: 12

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Ala Lys Ser Arg Phe Gly Leu Pro Ile Tyr Val Pro Glu
        35                  40                  45

Arg Glu Ala Pro Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Asp
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

His Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Val Gln Arg Phe Gln Ser Glu Ser Arg Val Leu Leu Arg Gln Ala
            355                 360                 365

Asn Asp Asn Arg Gln
    370

<210> SEQ ID NO 13
<211> LENGTH: 373
<212> TYPE: PRT
<213> ORGANISM: Escherichia coli

<400> SEQUENCE: 13

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Pro Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
            115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

His Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

```
Tyr Ala Gln Arg Leu Gln Ser Glu Ser Arg Val Leu Leu Arg Gln Ala
        355                 360                 365

Asn Asp Asn Arg Gln
    370

<210> SEQ ID NO 14
<211> LENGTH: 373
<212> TYPE: PRT
<213> ORGANISM: Escherichia coli

<400> SEQUENCE: 14

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Gly Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Arg Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala His Gly Leu His Leu Ala Gly Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Gly Leu Phe Ala Gln Asp Pro Gln Leu Tyr Ala
    290                 295                 300

Asp Ile Ile Met Leu Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Gly
```

```
                    340                 345                 350
Tyr Ala Gln Arg Phe Gln Ser Glu Ser Arg Val Leu Leu Arg Gln Ala
            355                 360                 365

Asn Asp Asn Arg Gln
        370

<210> SEQ ID NO 15
<211> LENGTH: 373
<212> TYPE: PRT
<213> ORGANISM: Escherichia coli

<400> SEQUENCE: 15

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Leu Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Ser Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile His Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335
```

```
Gln Ala Phe Ile Asp Ser Phe Pro Lys Val Glu His Trp Phe Gly Asp
                340                 345                 350

Tyr Ala Gln Arg Leu Gln Ser Glu Ser Arg Val Leu Leu Arg Gln Ala
            355                 360                 365

Asn Asp Asn Arg Gln
        370

<210> SEQ ID NO 16
<211> LENGTH: 373
<212> TYPE: PRT
<213> ORGANISM: Escherichia coli

<400> SEQUENCE: 16

Met Val Ala Glu Leu Thr Ala Leu Arg Asp Gln Val Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Arg Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335
```

```
Gln Ala Phe Ile Asp Ser Phe Arg Lys Val Glu His Trp Phe Gly Asp
            340                 345                 350
Tyr Ala Gln Arg Leu Gln Ser Glu Ser Arg Val Leu Leu Arg Gln Ala
        355                 360                 365
Asn Asp Asn Arg Gln
    370

<210> SEQ ID NO 17
<211> LENGTH: 373
<212> TYPE: PRT
<213> ORGANISM: Escherichia coli

<400> SEQUENCE: 17

Met Val Ala Glu Leu Thr Ala Leu Arg Asp Gln Val Asp Glu Val Asp
1               5                   10                  15
Lys Ala Leu Leu Asn Leu Leu Ala Lys Arg Leu Glu Leu Val Ala Glu
            20                  25                  30
Val Gly Glu Val Lys Ser Arg Phe Gly Leu Pro Ile Tyr Val Pro Glu
        35                  40                  45
Arg Glu Ala Ser Met Leu Ala Ser Arg Arg Ala Glu Ala Glu Ala Leu
    50                  55                  60
Gly Val Pro Pro Asp Leu Ile Glu Asp Val Leu Arg Arg Val Met Arg
65                  70                  75                  80
Glu Ser Tyr Ser Ser Glu Asn Asp Lys Gly Phe Lys Thr Leu Cys Pro
                85                  90                  95
Ser Leu Arg Pro Val Val Ile Val Gly Gly Gly Gln Met Gly Arg
            100                 105                 110
Leu Phe Glu Lys Met Leu Thr Leu Ser Gly Tyr Gln Val Arg Ile Leu
        115                 120                 125
Glu Gln His Asp Trp Asp Arg Ala Ala Asp Ile Val Ala Asp Ala Gly
    130                 135                 140
Met Val Ile Val Ser Val Pro Ile His Val Thr Glu Gln Val Ile Gly
145                 150                 155                 160
Lys Leu Pro Pro Leu Pro Lys Asp Cys Ile Leu Val Asp Leu Ala Ser
                165                 170                 175
Val Lys Asn Gly Pro Leu Gln Ala Met Leu Val Ala His Asp Gly Pro
            180                 185                 190
Val Leu Gly Leu His Pro Met Phe Gly Pro Asp Ser Gly Ser Leu Ala
        195                 200                 205
Lys Gln Val Val Val Trp Cys Asp Gly Arg Lys Pro Glu Ala Tyr Gln
    210                 215                 220
Trp Phe Leu Glu Gln Ile Gln Val Trp Gly Ala Arg Leu His Arg Ile
225                 230                 235                 240
Ser Ala Val Glu His Asp Gln Asn Met Ala Phe Ile Gln Ala Leu Arg
                245                 250                 255
His Phe Ala Thr Phe Ala Tyr Gly Leu His Leu Ala Glu Glu Asn Val
            260                 265                 270
Gln Leu Glu Gln Leu Leu Ala Leu Ser Ser Pro Ile Tyr Arg Leu Glu
        275                 280                 285
Leu Ala Met Val Gly Arg Leu Phe Ala Gln Asp Pro Gln Leu Tyr Ala
    290                 295                 300
Asp Ile Ile Met Leu Ser Glu Arg Asn Leu Ala Leu Ile Lys Arg Tyr
305                 310                 315                 320
Tyr Lys Arg Phe Gly Glu Ala Ile Glu Leu Leu Glu Gln Gly Asp Lys
```

```
                        325                 330                 335
Gln Ala Phe Ile Asp Ser Phe Arg Lys Val Glu His Trp Phe Gly Asp
                340                 345                 350
Tyr Val Gln Arg Phe Gln Ser Glu Ser Arg Val Leu Leu Arg Gln Ala
            355                 360                 365
Asn Asp Asn Arg Gln
        370

<210> SEQ ID NO 18
<211> LENGTH: 373
<212> TYPE: PRT
<213> ORGANISM: Escherichia coli

<400> SEQUENCE: 18

Met Val Ala Glu Leu Thr Ala Leu Arg Asp Gln Ile Asp Glu Val Asp
1               5                   10                  15
Lys Ala Leu Leu Asn Leu Leu Ala Lys Arg Leu Glu Leu Val Ala Glu
            20                  25                  30
Val Gly Glu Val Lys Ser Arg Phe Gly Leu Pro Ile Tyr Val Pro Glu
        35                  40                  45
Arg Glu Ala Ser Met Leu Ala Ser Arg Arg Ala Glu Ala Glu Ala Leu
    50                  55                  60
Gly Val Pro Pro Asp Leu Ile Glu Asp Val Leu Arg Arg Val Met Arg
65                  70                  75                  80
Glu Ser Tyr Ser Ser Glu Asn Asp Lys Gly Phe Lys Thr Leu Cys Pro
                85                  90                  95
Ser Leu Arg Pro Val Val Ile Gly Gly Gly Gln Met Gly Arg
            100                 105                 110
Leu Phe Glu Lys Met Leu Thr Leu Ser Gly Tyr Gln Val Arg Ile Leu
        115                 120                 125
Glu Gln His Asp Trp Asp Arg Ala Ala Asp Ile Val Ala Asp Ala Gly
    130                 135                 140
Met Val Ile Val Ser Val Pro Ile His Val Thr Glu Gln Val Ile Gly
145                 150                 155                 160
Lys Leu Pro Pro Leu Pro Lys Asp Cys Ile Leu Val Asp Leu Ala Ser
                165                 170                 175
Val Lys Asn Gly Pro Leu Gln Ala Met Leu Val Ala His Asp Gly Pro
            180                 185                 190
Val Leu Gly Leu His Pro Met Phe Gly Pro Asp Ser Gly Ser Leu Ala
        195                 200                 205
Lys Gln Val Val Val Trp Cys Asp Gly Arg Lys Pro Glu Ala Tyr Gln
    210                 215                 220
Trp Phe Leu Glu Gln Ile Gln Val Trp Gly Ala Arg Leu His Arg Ile
225                 230                 235                 240
Ser Ala Val Glu His Asp Gln Asn Met Ala Phe Ile Gln Ala Leu Arg
                245                 250                 255
His Phe Ala Thr Phe Ala Tyr Gly Leu His Leu Ala Glu Glu Asn Val
            260                 265                 270
Gln Leu Glu Gln Leu Leu Ala Leu Ser Ser Pro Ile Tyr Arg Leu Glu
        275                 280                 285
Leu Ala Met Val Gly Arg Leu Phe Ala Gln Asp Pro Gln Leu Tyr Ala
    290                 295                 300
Asp Ile Ile Met Leu Ser Glu Arg Asn Leu Ala Leu Ile Lys Arg Tyr
305                 310                 315                 320
```

```
Tyr Lys Arg Phe Gly Glu Ala Ile Glu Leu Leu Gly Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Leu Gln Ser Glu Ser Arg Val Leu Leu Arg Gln Ala
        355                 360                 365

Asn Asp Asn Arg Gln
    370
```

<210> SEQ ID NO 19
<211> LENGTH: 373
<212> TYPE: PRT
<213> ORGANISM: Escherichia coli

<400> SEQUENCE: 19

```
Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Gly
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asp Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320
```

```
Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Ala Gln Arg Leu Gln Ser Glu Ser Arg Val Leu Leu Arg Gln Ala
        355                 360                 365

Asn Asp Asn Arg Gln
    370

<210> SEQ ID NO 20
<211> LENGTH: 372
<212> TYPE: PRT
<213> ORGANISM: Escherichia coli

<400> SEQUENCE: 20

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Met Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asp Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Leu Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Leu Ser Glu Arg Asn Leu Ala Leu Ile Lys Arg Tyr
```

```
              305                 310                 315                 320
Lys Arg Phe Gly Glu Ala Ile Glu Leu Leu Gly Gln Gly Asp Lys Gln
                    325                 330                 335

Ala Phe Ile Asp Ser Phe Arg Lys Val Glu His Trp Phe Gly Asp Tyr
            340                 345                 350

Ala Arg Arg Phe Gln Ser Glu Ser Arg Val Leu Leu Arg Gln Ala Asn
                355                 360                 365

Asp Asn Arg Gln
        370

<210> SEQ ID NO 21
<211> LENGTH: 373
<212> TYPE: PRT
<213> ORGANISM: Escherichia coli

<400> SEQUENCE: 21

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Ile Leu Ala Ser Arg Arg Ala Glu Ala Glu Ala Leu
    50                  55                  60

Gly Val Pro Pro Asp Leu Ile Glu Asp Val Leu Arg Arg Val Thr Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300
```

```
Asp Ile Ile Met Ser Ser Glu Arg Asn Leu Ala Leu Ile Lys Arg Tyr
305                 310                 315                 320

His Lys Arg Phe Gly Glu Ala Ile Glu Leu Leu Glu Gln Gly Asp Lys
            325                 330                 335

Gln Ala Phe Ile Asp Ser Phe Arg Lys Val Glu His Trp Phe Gly Asp
            340                 345                 350

Tyr Ala Gln Arg Phe Gln Ser Glu Ser Arg Val Leu Leu Arg Gln Ala
        355                 360                 365

Asn Asp Asn Arg Gln
        370
```

<210> SEQ ID NO 22
<211> LENGTH: 1122
<212> TYPE: DNA
<213> ORGANISM: Escherichia coli

<400> SEQUENCE: 22

```
atggttgctg aattgaccgc attacgcgat caaattgatg aagtcgataa agcgctgctg      60
aatttattag cgaagcgtct ggaactggtt gctgaagtgg gcgaggtgaa aagccgcttt     120
ggactgccta tttatgttcc ggagcgcgag gcatctatgt tggcctcgcg tcgtgcagag     180
gcggaagctc tgggtgtacc gccagatctg attgaggatg ttttgcgtcg ggtgatgcgt     240
gaatcttact ccagtgaaaa cgacaaagga tttaaaacac tttgtccgtc actgcgtccg     300
gtggttatcg tcggcggtgg cggtcagatg ggacgcctgt tcgagaagat gctgaccctc     360
tcgggttatc aggtgcggat tctggagcaa catgactggg atcgagcggc tgatattgtt     420
gccgatgccg aatggtgat tgttagtgtg ccaatccacg ttactgagca agttattggc      480
aaattaccgc ctttaccgaa agattgtatt ctggtcgatc tggcatcagt gaaaaatggg     540
ccattacagg ccatgctggt ggcgcatgat ggtccggtgc tggggctaca cccgatgttc     600
ggtccggaca gcgtagcct ggcaaagcaa gttgtggtct ggtgtgatgg acgtaaaccg      660
gaagcatacc aatggtttct ggagcaaatt caggtctggg cgctcggct gcatcgtatt      720
agcgccgtcg agcacgatca gaatatggcg tttattcagg cactgcgcca ctttgctact     780
tttgcttacg gctgcacct ggcagaagaa atgttcagc ttgagcaact tctggcgctc       840
tcttcgccga tttaccgcct tgagctggcg atggtcgggc gactgtttgc tcaggatccg     900
cagctttatg ccgacatcat tatgtcgtca gagcgtaatc tggcgttaat caaacgttac     960
tataagcgtt tcggcgaggc gattgagttg ctggagcagg cgataagca ggcgtttatt     1020
gacagtttcc gcaaggtgga gcactggttc ggcgattacg cacagcgttt tcagagtgaa    1080
agccgcgtgt tattgcgtca ggcgaatgac aatcgccagt aa                       1122
```

<210> SEQ ID NO 23
<211> LENGTH: 1122
<212> TYPE: DNA
<213> ORGANISM: Escherichia coli

<400> SEQUENCE: 23

```
atggttgctg aattgaccgc attacgcgat caaattgatg aagtcgataa agcgctgctg      60
aatttattag cgaagcgtct gggactggtt gctgaagtgg gcgaggtgaa aagccgcttt     120
ggactgccta ttcatgttcc ggagcgcgag gcatctatgt tggcctcgcg tcgtgcagag     180
gcggaagctc tgggtgtacc gccagatctg attgaggatg ttttgcgtcg ggtgatgcgt     240
gaatcttact ccagtgaaaa cgacaaagga tttaaaacac tttgtccgtc actgcgtccg     300
```

-continued

| | |
|---|---|
| gtggttatcg tcggcggtgg cggtcagatg ggacgcctgt tcgagaagat gctgaccctc | 360 |
| tcgggttatc aggtgcggat tctggagcaa catgactggg atcgagcggc tgatattgtt | 420 |
| gccgatgccg aatggtgat tgttagtgtg ccaatccacg ttactgagca agttattggc | 480 |
| aaattaccgc ctttaccgaa agattgtatt ctggtcgatc tggcatcagt gaaaaatggg | 540 |
| ccattacagg ccatgctggt ggcgcatgat ggtccggtgc tggggctaca cccgatgttc | 600 |
| ggtccggaca gcggtagcct ggcaaagcaa gttgtggtct ggtgtgatgg acgtaaaccg | 660 |
| gaagcatacc aatggtttct ggagcaaatt caggtctggg gcgctcggct gcatcgtatt | 720 |
| agcgccgtcg agcacgatca gaatatggcg tttattcagg cactgcgcca ctttgctact | 780 |
| tttgctcacg gctgcacct ggcagaagaa aatgttcagc ttgagcaact tctggtgctc | 840 |
| tcttcgccga tttaccgcct tgagctgcg atggtcgggc gactgtttgc tcaggatccg | 900 |
| cagctttatg ccgacatcat tatgtcgtca gagcgtaatc tggcgttaat caaacgttac | 960 |
| tataagcgtt tcggcgaggc gattgagttg ctggagcagg gcgataagca ggcgtttatt | 1020 |
| gacagtttcc gcaaggtgga gcactggttc ggcgattacg cacagcgttt tcagagtgaa | 1080 |
| agccgcgtgt tattgcgtca ggcgaatgac aatcgccagt aa | 1122 |

<210> SEQ ID NO 24
<211> LENGTH: 1122
<212> TYPE: DNA
<213> ORGANISM: Escherichia coli

<400> SEQUENCE: 24

| | |
|---|---|
| atggttgctg aattgaccgc attacgcgat caaattgatg aagtcgataa agcgctgctg | 60 |
| aatttattag cgaagcgtct ggaactggtt gctgaagtgg gcgaggtgaa aagccgcttt | 120 |
| ggactgccta tttatgttcc ggagcgcgag gcatctatgt tggcctcgcg tcgtgcagag | 180 |
| gcggaagctc tgggtgtacc gccagatctg attgaggatg ttttgcgtcg ggtgatgcgt | 240 |
| gaatcttact ccagtggaaa cgacaaagga tttaaaacac tttgtccgtc actgcgtccg | 300 |
| gtggttatcg tcggcggtgg cggtcagatg ggacgcctgt tcgagaagat gctgaccctc | 360 |
| tcgggttatc aggtgcggac tctggagcaa catgactggg atcgagcggc tgatattgtt | 420 |
| gccgatgccg aatggtgat tgttagtgtg ccgatccacg ttactgagca agttattggc | 480 |
| aaattaccgc ctctaccgaa agattgtatt ctggtcgatc tggcatcagt gaaagatggg | 540 |
| ccattacagg ccatgctggt ggcgcacgat ggtccggtgc tggggctaca cccgatgttc | 600 |
| ggtccggaca gcggtagcct ggcaaagcaa gttgtggtct ggtgtgatgg acgtaaaccg | 660 |
| gaagcatacc aatggtttct ggagcaaatt caggtctggg gcgctcggct gcatcgtatt | 720 |
| agcgccgtcg agcacgatca gaatatggcg tttattcagg cactgcgtca ctttgctact | 780 |
| tttgcttacg gctgcacct ggcagaagaa aatgttcagc ttgagcaact tctggcgctc | 840 |
| ttttcgccga tttaccgcct tgagctgcg atggtcgggc gactgtttgc tcaggatccg | 900 |
| cagctttgtg ccgacatcat tatgtcgtca gagcgtaatc tggcgttaat caaacgttac | 960 |
| tataagcgtt tcggcgaggc gattgagttg ctggagcagg gcgataagca ggcgtttatt | 1020 |
| gacagtttcc gcaaggtgga gcactggttc ggcgattacg cacagcgttt tcagagtgaa | 1080 |
| agccgcgtgt tattgcgtca ggcgaatgac aatcgccagt aa | 1122 |

<210> SEQ ID NO 25
<211> LENGTH: 1122
<212> TYPE: DNA
<213> ORGANISM: Escherichia coli

<400> SEQUENCE: 25

```
atggttgctg aattgaccgc attacgcgat caaattgatg aagtcgataa agcgctgctg      60
aatttattag cgaagcgtct ggaactggtt gctgaagtgg gcgaggtgaa aagccgcttt     120
ggactgccta tttatgttcc ggagcgcgag gcatctatgt tggcctcgcg tcgtgcagag     180
gcggaagctc tggtgtacc gccagatctg attgaggatg ttttgcgtcg ggtgatgcgt      240
gaatcttact ccagtgaaaa cgacaaagaa tttaaaacac tttgtccgtc actgcgtccg     300
gtggttatcg tcggcggtgg cggtcagatg ggacgcctgt tcgagaagat gctgaccctc     360
tcgggttatc aggtgcggat tctggagcaa catgactggg atcgggcggc tgatattgtt     420
gccgatgccg aatggtgat tgttagtgtg ccaatccacg ttactgagca agttattggc      480
aaattaccgc ctttaccgaa agattgtatt ctggtcgatc tggcatcagt gaaaaatggg     540
ccattacagg ccatgctggt ggcgcatgat ggtccggtgc tggggctaca cccgatgttc     600
ggtccggaca gcggtagcct ggcaaagcaa gttgtggtct ggtgtgacgg acgtaaaccg     660
gaagcatacc aatggtttct ggagcaaatt caggtctggg gcgctcggct gcatcgtatt     720
agcgccgtcg agcacgatca gaatatggcg tttattcagg cactgcgcca ctttgctact     780
tttgcttgcg ggctgcacct ggcagaagag aatgttcagc ttgagcaact tctggcgctc     840
tcttcgccga tttaccgcct tgagctggcg atggtcgggc gactgtttgc tcaggatccg     900
cagctttatg ccgacatcat tatgtcgtca gagcgtaatc tggcgttaat caaacgttac     960
tataagcgtt tcggcgaggc gattgagttg ctggagcagg cggtaagca ggcgtttatt     1020
gacagtttcc gcaaggtgga gcactggttc ggcgattacg cacagcgttt tcagagtgaa    1080
agccgcgtgt tattgcgtca ggcgaatgac aatcgccagt aa                        1122
```

<210> SEQ ID NO 26
<211> LENGTH: 1122
<212> TYPE: DNA
<213> ORGANISM: Escherichia coli

<400> SEQUENCE: 26

```
atggttgctg aattgaccgc attacgcgat caaattgatg aagtcgataa agcgctgctg      60
aatttattag cgaagcgtct ggaactggtt gctgaagtgg gcgaggtgaa aagccgcttt     120
ggactgccta tttatgttcc ggagcgcgag gcatctatgt tggcctcgcg tcgtgcagag     180
gcggaagctc tggtgtacc gccagatctg attgaggatg ttttgcgtcg ggtgatgcgt      240
gaatcttact ccagtgaaaa cgacaaagga tttaaaacac tttgtccgtc actgcgtccg     300
gtggttatcg tcggcggtgg cggtcagatg ggacgcctgt tcgagaagat gctgaccctc     360
tcgggttatc aggtgcggat tctggagcaa catgactggg atcgagcggc tgatattgtt     420
gccgatgccg aatggtgat tgttagtgtg ccaatccacg ttactgagca agttattggc      480
aaattaccgc ctttaccgaa agattgtatt ctggttgatc tggcatcagt gaaaaatggg     540
ccattacagg ccatgctggt ggcgcatgat ggtccggtgc tggggctaca cccgatgttc     600
ggtccggaca gcggtagcct ggcaaagcaa gttgtggtct ggtgtgatgg acgtaaaccg     660
gaagcatacc aatggtttct ggagcaaatt caggtctggg gcgctcggct gcatcgtatt     720
agcgccgtcg agcacgatca gaatatggcg tttattcagg cactgcgcca ctttgctact     780
tttgcttacg ggctgcacct ggcagaagaa aatgttcagc ttgagcaact tctggcgctc     840
tcttcgccga tttaccgcct tgagctggcg atggtcgggc gactgtttgc tcaggatccg     900
```

```
cagctttatg ccgacatcat tatgtcgtca gagcgtaatc tggcgttaat caaacgttac      960
tataagcgtt tcggcgaggc gattgagttg ctggagcagg gcgataagca ggcgtttatt     1020
gacagtttcc gcaaggtgga gcactggttc ggcgattacg cacagcgtct tcagagtgaa     1080
agccgcgtgt tattgcgtca ggcgaatgac aatcgccagt aa                        1122

<210> SEQ ID NO 27
<211> LENGTH: 1122
<212> TYPE: DNA
<213> ORGANISM: Escherichia coli

<400> SEQUENCE: 27
atggttgctg aattgaccgc attacgcgat caaattgatg aagtcgataa agcgctgctg       60
aatttattag cgaagcgtct ggaactggtt gctgaagtgg gcgaggtgga aagccgcttt     120
ggactgccta tttatgtttc ggagcgcgag gcatctatgt tggcctcgcg tcgtgcagag     180
gcggaagctc tgggtgtacc gccagatctg attgaggatg ttttgcgtcg ggtgatgcgt     240
gaatcttact ccagtgaaaa cgacaaagga tttaaaacac tttgtccgtc actgcgtccg     300
gtggttatcg tcgcggtgg cggccagatg ggacgcctgt tcgagaagat gctgaccctc     360
tcgggttatc aggtgcggat tctggagcaa catgactggg atcgagcggc tgatattgtt     420
gccgatgccg aatggtgat tgttagtgtg ccaatccacg ttactgagca agttattggc     480
aaattaccgc ctttaccgaa agattgtatt ctggtcgatc tggcatcagt gaaaaatagg     540
ccattacagg ccatgctggt ggcgcatgat ggtccggtgc tggggctaca cccgatgttc     600
ggtccggaca gcggtagcct ggcaaagcaa gttgtggtct ggtgtgatgg acggaaaccg     660
gaagcatacc aatggtttct ggagcaaatt caggtctggg gcgctcggct gcatcgtatt     720
agcgccgtcg agcacgatca gaatatggcg tttattcagg cactgcgcca ctttgctact     780
tttgcttacg ggctgcacct ggcagaagaa aatgttcagc ttgagcaact tctggcgctc     840
tcttcgccga tttaccgcct tgagctggcg atggtcgggc gactgtttgc tcaggatccg     900
cagctttatg ccgacatcat tatgtcgtca gagcgtaatc tggcgttaat caaacgttac      960
tataagcgtt tcggcgaggc gattgagttg ctggagcagg gcgataagca ggcgtttatt     1020
gacagtttcc gcaaggtgga gcactggttc ggcgattacg cacagcgtct tcagagtgaa     1080
agccgcgtgt tattgcgtca ggcgaatgac aatcgccagt aa                        1122

<210> SEQ ID NO 28
<211> LENGTH: 1122
<212> TYPE: DNA
<213> ORGANISM: Escherichia coli
<220> FEATURE:
<221> NAME/KEY: misc_feature
<222> LOCATION: (1101)..(1101)
<223> OTHER INFORMATION: n is a, c, g, or t

<400> SEQUENCE: 28
atggttgctg aattgaccgc attacgcgat caaattgatg aagtcgataa agcgctgctg       60
aatttattag cgaagcgtct ggaactggtt gctgaagtgg gcgaggtgaa aagccgcttt     120
ggactgccta tttatgtttc ggagcgcgag gcatctatgt tggcctcgcg tcgtgcagag     180
gcggaagctc tgggtgtacc gccagatctg attgaggatg ttttgcgtcg ggtgatgcgt     240
gaatcttgct ccagtgaaag cgacaaagga tttaaaacac tttgtccgtc actgcgtccg     300
gtggttatcg tcgcggtgg cggtcagatg ggacgcctgt tcgagaagat gctgaccctc     360
tcgggttatc aggtgcggat tctggagcaa catgactggg atcgagcggc tgatattgtt     420
```

```
gccgatgccg aatggtgat tgttagtgtg ccaatccacg ttactgagca ggttattggc    480
aagttaccgc ctttaccgaa agattgtatt ctggtcgatc tggcatcagt gaaaaatggg    540
ccattacagg ccatgctggt ggcgcatgat ggtccggtgc tggggctaca cccgatgttc    600
ggtccggaca gcggtagcct ggcaaagcaa gtcgtggtct ggtgtgatgg acgtaaaccg    660
gaagcatacc aatggtttct ggagcaaatt caggtctggg cgctcggct gcatcgtatt      720 agcgccgtcg agcacgatca gaatatggcg tttattcagg cactgcgcca ctttgctgct    780
tttgcttacg ggctgcacct ggcagaagaa aatgttcagc ttgagcaact tctggcgctc    840
tcttcgccga tttacccct tgagctggcg atggtcgggc gactgtttgc tcaggatccg    900
cagctttatg ccgacatcat tatgtcgtca gagcgtaatc tggcgttaat caaacgttac    960
tataagcgtt tcggcgaggc gattgagttg caggagcagg gcgataagca ggccttaat   1020 gacagtttcc ccaaggtgga gcactggttc ggcgattacg cacagcgtct tcagagtgaa  1080
agccgcgtgt tattgcgtca ngcgaatgac aatcgccagt aa                         1122

<210> SEQ ID NO 29
<211> LENGTH: 1122
<212> TYPE: DNA
<213> ORGANISM: Escherichia coli

<400> SEQUENCE: 29
atggttgctg aattgaccgc attacgcgat cgaattgatg aagtcgataa agcgctgctg     60
aatttattag cgaagcgtct ggaactggct gctgaagtgg gcgaggtgaa aagccgcttt    120
ggactgccta tttatgttcc ggagcgcgag gcatctatgt tggcctcgcg tcgtgcagag   180
gcggaagctc tgggtgtacc gccagatctg attgaggatg ttttgcgtcg ggtgatgcgt    240
gaatcttact ccagtgaaaa cgacaaagga tttaaaacac tttgtccgtc actgcgtccg   300
gtggttatcg tcgcggtgg cggtcagatg ggacgcctgt tcgagaagat gctgaccctc     360
tcgggttatc aggtgcggat tctggagcaa catgactggg atcgagcggc tgatattgtt    420
gccgatgccg aatggtgat tgttagtgtg ccaatccacg ttactgagca agttattggc    480
aaattaccgc ctttaccgaa agattgtatt ctggtcgatc tggcatcagt gaaaaatggg    540
ccattacagg ccatgctggt ggcgcatgat ggtccggtgc tggggctaca cccgatgttc    600
ggtccggaca gcggtagcct ggcaaagcaa gttgtggtct ggtgtgatgg acgtaaaccg    660
gaagcatacc aatggtttct ggagcaaatt caggtctggg cgctcggct gcatcgtatt      720 agcgccgtcg agcacgatca gaatatggcg tttattcagg cactgcgcca ctttgctact    780
tttgctcacg ggctgcacct ggcagaagaa aatgttcagc ttgagcaact tctggcgctc    840
tcttcgccga tttaccgcct tgagctggcg atggtcgggc gactgtttgc tcaggatccg    900
cagctttatg ccgacatcat tatgtcgtca gagcgtaatc tggcgttaat caaacgttac    960
tataagcgtt tcggcgaggc gattgagttg ctggagcagg gcgataagca ggcgtttatt  1020
gacagtttcc gcaaggtgga gcactggttc ggcgattacg cacagcgttt tcagagtgaa  1080
agccgcgtgt tattgcgtca ggcgaatgac aatcgccagt aa                         1122

<210> SEQ ID NO 30
<211> LENGTH: 1122
<212> TYPE: DNA
<213> ORGANISM: Escherichia coli

<400> SEQUENCE: 30
```

```
atggttgctg aattgaccgc attacgcgat caaattgatg aagtcgacaa agcgctgctg      60
aatttattag cgaagcgtct ggaactggtt gctgaagtgg gcgaggtgaa aagccgcttt     120
ggactgccta tttatgttcc ggagcgcgag gcatctatgt tggcctcgcg ccgtgcagag     180
gcggaagctc tgggtgtacc gccagatctg attgaggatg ttttgcgtcg ggtgatgcgt     240
gaatcttact ccagtgaaaa cgacaaagga tttaaaacac tttgtccgtc actgcgtccg     300
gtggttatcg tcgcggtgg cggtcagatg ggacgcctgt tcgagaagat gctgaccctc     360
tcgggttatc aggtgcggat tctggagcaa catgactggg atcgagcggc tgatattgtt     420
gccgatgccg aatggtgat tgttagtgtg ccaatccacg ttactgagca agttattggc      480
aaattaccgc ctttaccgaa agattgtatt ctggtcgatc tggcatcagt gaaaaatggg     540
ccattacagg ccatgctggt ggcgcatgat ggtccggtgc tggggctaca cccgatgttc     600
ggtccggaca gcggtagcct ggcaaagcaa gttgtggtct ggtgtgatgg acgtaaaccg     660
gaagcatacc aatggtttct ggagcaaatt caggtctggg gcgctcggct gcatcgtatt     720
agcgccgtcg agcacgatca gaatatggcg ttcattcagg cactgcgcca ctttgctact     780
tttgctcacg gctgcacct ggcagaagaa aatgttcagc ttgagcaact tctggcgctc      840
tcttcgccga tttaccgcct tgagctggcg atggtcgggc gactgtttgc tcaggatccg     900
cagctttatg ccgacatcat tatgtcgtca gagcgtaatc tggcgttaat caaacgttac     960
tataagcgtt tcggcgaggc gattgagttg ctggagcagg gcgataagca ggcgtttatt    1020
gacagtttcc gcaaggtgga gcactggttc ggcgattacg cacagcgttt tcagagtgaa    1080
agccgcgtgt tattgcgtca ggcgaatgac aatcgccagt aa                       1122

<210> SEQ ID NO 31
<211> LENGTH: 1122
<212> TYPE: DNA
<213> ORGANISM: Escherichia coli

<400> SEQUENCE: 31
atggttgctg aattgaccgc attacgcgat caaattgatg aagtcgataa agcgctgctg      60
aatttattag cgaagcgtct ggaactggtt gctgaagtgg gcgaggtgaa aagccgcttt     120
ggactgccta tttatgttcc ggagcgcgag gcatctatgt tggcctcgcg tcgtgcagag     180
gcggaagctc tgggtgtacc gccagatctg attgaggatg ttttgcgtcg ggtgatgcgt     240
gaatcttact ccagtgaaaa cgacaaagga tttaaaacac tttgtccgtc actgcgtccg     300
gtggttatcg tcgcggtgg cggtcagatg ggacgcctgt tcgagaagat gctgaccctc     360
tcgggttatc aggtgcggat tctggagcaa catgactggg atcgagcggc tgacattgtt     420
gccgatgccg aatggtgat tgttagtgtg ccaatccacg ttactgagca agttattggc      480
aaattaccgc ctttaccgaa agattgtatt ctggtcgatc tggcatcagt gaaaaatggg     540
ccgttacagg ccatgctggt ggcgcatgat ggtccggtgc tggggctaca cccgatgttc     600
ggtccggaca gcggtagcct ggcaaagcaa gttgtggtct ggtgtgatgg acgtaaaccg     660
gaagcatacc aatggtttct ggagcaaatt caggtctggg gcgctcggct gcactgtatt     720
agcgccgtcg agcacgatca gagtatggcg tttattcagg cactgcgcca ctttgctact     780
tttgcttacg gctgcacct ggcagaagaa aatgttcagc ttgagcgact tctggcgctc      840
tcttcgctga tttaccgcct tgagctggcg atggtcgggc gactgtttgc tcgggatccg     900
cagctttatg ccgacatcat tatgtcgtca gagcgtaatc tggcgttaat caaacgttac     960
tataagcgtt tcggcgaggc gattgagttg ctggagcagg gcgataagca ggcgtttatt    1020
```

```
gacagtttcc gcaaggtgga gcactggttc ggcgattacg cacagcgttt tcagagtgaa   1080
agccgcgtgc tattgcgtca ggcgaatgac aatcgccagt aa                      1122

<210> SEQ ID NO 32
<211> LENGTH: 1122
<212> TYPE: DNA
<213> ORGANISM: Escherichia coli

<400> SEQUENCE: 32
atggttgctg aattgaccgc attatgcgat caaattgatg aagtcgataa agcgctgctg     60
aatttattag cgaagcgtct ggaactggtt gctgaagtgg gcgaggtgaa aagccgcttt    120
ggactgccta tttatgttcc ggagcgcgag gcatctatgt tggcctcgcg tcgtgcagag    180
gcggaagctc tgggtgtacc gccagatctg attgaggatg ttttgcgtcg agtgatgcgt    240
gaatcttacc ccagtgaaaa cgacaaagga tttaaaacac tttgtccgtc actgcgtccg    300
gtggttatcg tcggcggtgg cggtcagatg ggacgcctgt tcgagaagat gctgaccctc    360
tcgggttatc aggtgcggat tctggagcaa catgactggg atcgagcggc tgatattgtt    420
gccgatgccg gaatggtgat tgttagtgtg ccaatccacg ttactgagca gttattggc     480 aaattaccgc ctttaccgaa agattgtatt ctggtcgatc tggcatcagt gaaaaatggg    540
ccgttacagg ccatgctggt ggcgcatgat ggtccggtgc tggggctaca cccgatgttc    600
ggtccggaca cgtagcct ggcaaagcaa gttgtggtct ggtgtgatgg acgtaaaccg       660
gaagcatacc aatggtttct ggagcaaatt caggtctggg cgctcggct gcatcgtatt     720 agcgccgtcg agcacgatca gagtatggcg tttattcagg cactgcgcca ctttgctact    780
tttgcttacg ggctgcacct ggcagaagaa atgttcagc ttgagcgact tttggcgctc     840
tcttcgccga tttaccgcct tgagctggcg atggttgggc gactgtttgc tcgggatccg    900
cagctttatg ccgacatcat tatgttgtca gagcgtaatc tggcgttaat caaacgttac    960
tataagcgtt tcggcgaggc gattgagttg ctggagcagg gcgataagca ggcgtttatt   1020
gacagtttcc gcaaggtgga gcactggttc ggcgattacg cacagcgtct tcagagtgaa   1080
agccgcgtgt tattgcgtca ggcgaatgac aatcgccagt aa                      1122

<210> SEQ ID NO 33
<211> LENGTH: 1122
<212> TYPE: DNA
<213> ORGANISM: Escherichia coli

<400> SEQUENCE: 33
atggttgctg aattgaccgc attacgcgat caaattgatg aagtcgataa agcgctgctg     60
aatttattag cgaagcgtct ggaactggtt gctgaagtgg gcgaggcgaa aagccgcttt    120
ggactgccta tttatgttcc ggagcgcgag gcacctatgt tggcctcgcg tcgtgcagag    180
gcggaagctc tgggtgtacc gccagatctg attgaggatg ttttgcgtcg ggtgatgcgt    240
gaatcttact ccagtgaaaa cgacaaagga tttaaaacac tttgtccgtc actgcgtccg    300
gtggttatcg tcggcggtgg cggtcagatg ggacgcctgt tcgagaagat gctgaccctc    360
tcgggttatc aggtgcggat tctggagcaa catgactggg atcgagcggc tgatattgtt    420
gccgatgccg gaatggtgat tgttagtgtg ccaatccacg ttactgagca gttattggc     480 aaattaccgc ctttaccgaa agattgtatt ctggtcgatc tggcatcagt gaaaaatggg    540
ccattacagg ccatgctggt ggcgcatgat ggtccggtgc tggggctaca cccgatgttc    600
```

```
ggtccggaca gcggtagcct ggcaaagcaa gttgtggtct ggtgtgatgg acgtaaaccg      660
gaagcatacc aatggttcct ggagcaaatt caggtctggg gcgctcggct gcatcgtatt      720
agcgccgtcg agcacgatca gaatatggcg tttattcagg cactgcgcca ctttgctact      780
tttgcttacg ggctgcacct ggcagaagaa aatgttcagc ttgagcaact tctggcgctc      840
tcttcgccga tttaccgcct tgacctggcg atggtcgggc gactgtttgc tcaggatccg      900
cagctttatg ccgacatcat tatgtcgtca gagcgtaatc tggcgttaat caaacgttac      960
cataagcgtt tcggcgaggc gattgagttg ctggagcagg gcgataagca ggcgtttatt     1020
gacagtttcc gcaaggtgga gcactggttc ggcgattacg tacagcgttt tcagagtgaa     1080
agccgcgtgt tattgcgtca ggcgaatgac aatcgccagt aa                        1122
```

<210> SEQ ID NO 34
<211> LENGTH: 1122
<212> TYPE: DNA
<213> ORGANISM: Escherichia coli

<400> SEQUENCE: 34

```
atggttgctg aattgaccgc attacgcgat caaattgatg aagtcgataa agcgctgctg       60
aatttattag cgaagcgtct ggaactggtt gctgaagtgg gcgaggtgaa aagccgcttt      120
ggactgccta tttatgttcc ggagcgcgag gcatctatgt tggcctcgcg tcgtgcagag      180
gcggaagctc tgggtgtacc gccagatctg attgaggatg ttttgcgtcg ggtgatgcgt      240
gaaccttact ccagtgaaaa cgacaaagga tttaaaacac tttgtccgtc actgcgtccg      300
gtggttatcg tcggcggtgg cggtcagatg ggacgcctgt tcgagaagat gctgaccctc      360
tcgggttatc aggtgcggat tctggagcaa catgactggg atcgagcggc tgatattgtt      420
gccgatgccg aatggtgat  tgttagtgtg ccaatccacg ttactgagca agttattggc      480
aaattaccgc ctttaccgaa agattgtatt ctggtcgatc tggcatcagt gaaaaatggg      540
ccattacagg ccatgctggt ggcgcatgat ggtccggtgc tggggctaca cccgatgttc      600
ggtccggaca gcggtagcct ggcaaagcaa gttgtggtct ggtgtgatgg acgtaaaccg      660
gaagcatacc aatggtttct ggagcaaatt caggtctggg gcgctcggct gcatcgtatt      720
agcgccgtcg agcacgatca gaatatggcg tttattcagg cactgcgcca ctttgctact      780
tttgcttacg ggctgcacct ggcagaagaa aatgttcagc ttgagcaact tctggcgctc      840
tcttcgccga tttaccgcct tgagctggcg atggtcgggc gactgtttgc tcaggatccg      900
cagctttatg ccgacatcat tatgtcgtca gagcgtaatc tggcgttaat caaacgttac      960
cataagcgtt tcggcgaggc gattgagttg ctggagcagg gcgataagca ggcgtttatt     1020
gacagtttcc gcaaggtgga gcactggttc ggcgattacg cacagcgtct tcagagtgaa     1080
agccgcgtgt tattgcgtca ggcgaatgac aatcgccagt aa                        1122
```

<210> SEQ ID NO 35
<211> LENGTH: 1122
<212> TYPE: DNA
<213> ORGANISM: Escherichia coli

<400> SEQUENCE: 35

```
atggttgctg aattgaccgc attacgcgat caaattgatg aagtcgataa agcgctgctg       60
aatttattag cgaagcgtct ggaactggtt gctgaagtgg gcgaggtgaa aggccgcttt      120
ggactgccta tttatgttcc ggagcgcgag gcatctatgt tggcctcgcg tcgtgcagag      180
gcggaagctc tgggtgtacc gccagatctg attgaggatg ttttgcgtcg ggtgatgcgt      240
```

```
gaatcttact ccagtgaaaa cgacaaagga tttaaaacac tttgtccgtc actgcgtccg    300
gtggttatcg tcggcggtgg cggtcagatg ggacgcctgt tcgagaagat gctgaccctc    360
tcgggttatc aggtgcggat tctggagcaa catgactggg atcgagcggc tgatattgtt    420
gccgatgccg aatggtgat tgttagtgtg ccaatccacg ttactgagcg agttattggc     480
aaattaccgc ctttaccgaa agattgtatt ctggtcgatc tggcatcagt gaaaaatggg    540
ccattacagg ccatgctggt ggcgcatgat ggtccggtgc tggggctaca cccgatgttc    600
ggtccggaca gcgtagcct ggcaaagcaa gttgtggtct ggtgtgatgg acgtaaaccg     660
gaagcatacc aatggtttct ggagcaaatt caggtctggg gcgctcggct gcatcgtatt    720
agcgccgtcg agcacgatca gaatatggcg tttattcagg cactgcgcca ctttgctact    780
tttgctcacg ggctgcacct ggcaggagaa aatgttcagc ttgagcaact tctggcgctc    840
tcttcgccga tttaccgcct tgagctggcg atggtcgggg gactgtttgc tcaggatccg    900
cagctttatg ccgacatcat tatgttgtca gagcgtaatt tggcgttaat caagcgttac    960
tataagcgtt tcggcgaggc gattgagttg ctggagcagg gcgataagca ggcgtttatt   1020
gacagtttcc gcaaggtgga gcactggttc ggcggttacg cacagcgttt tcagagtgaa   1080
agccgcgtgt tattgcgtca ggcgaatgac aatcgccagt aa                      1122

<210> SEQ ID NO 36
<211> LENGTH: 1122
<212> TYPE: DNA
<213> ORGANISM: Escherichia coli

<400> SEQUENCE: 36
atggttgctg aattgaccgc attacgcgat caaattgatg aagtcgataa agcgctgctg     60
aatttattag cgaagcgtct ggaactggtt gctgaagtgg gcgaggtgaa aagccgcttt    120
ggactgccta tttatgttcc ggagcgcgag gcatctatgt tggcctcgcg tcgtgcagag    180
gcggaagctc tgggtgtacc gccagatctg attgaggatg ttttgcgtcg ggtgatgcgt    240
gaatcttact ccagtgaaaa cgacaaagga cttaaaacac tttgtccgtc actgcgtccg    300
gtggttatcg tcggcggtgg cggtcagatg ggacgcctgt tcgagaagat gctgaccctc    360
tcgggttatc aggtgcggat tctggagcaa catgactggg atcgagcggc tgatattgtt    420
gccgatgccg aatggtgat tgttagtgtg ccaatccacg ttactgagca agttattggc     480
aaattaccgc ctttaccgaa agattgtatt ctggtcgatc tggcatcagt gaaaagtggg    540
ccattacagg ccatgctggt ggcgcatgat ggtccggtgc tggggctaca cccgatgttc    600
ggtccggaca gcgtagcct ggcaaagcaa gttgtggtct ggtgtgatgg acgtaaaccg     660
gaagcatacc aatggtttct ggagcaaatt caggtctggg gcgctcggct gcatcgtatt    720
agcgccgtcg agcacgatca gaatatggcg tttattcagg cactgcgcca ctttgctact    780
tttgcttacg ggctgcacct ggcagaagaa aatgttcagc ttgagcaact tctggcgctc    840
tcttcgccga ttcaccgcct tgagctggcg atggtcgggc gactgtttgc tcaggatccg    900
cagctttatg ccgacatcat tatgtcgtca gagcgtaatc tggcgttaat caaacgttac    960
tataagcgtt tcggcgaggc gattgagttg ctggagcagg gcgataagca ggcgtttatt   1020
gacagtttcc ccaaggtgga gcactggttc ggcgattacg cacagcgtct tcagagtgaa   1080
agccgcgtgt tattgcgtca ggcgaatgac aatcgccagt aa                      1122

<210> SEQ ID NO 37
```

<211> LENGTH: 1122
<212> TYPE: DNA
<213> ORGANISM: Escherichia coli

<400> SEQUENCE: 37

| | |
|---|---|
| atggttgctg aattgaccgc attacgcgat caagttgatg aagtcgataa agcgctgctg | 60 |
| aatttattag cgaagcgtct ggaactggtt gctgaagtgg gcgaggtgaa aagccgcttt | 120 |
| ggactgccta tttatgttcc ggagcgcgag gcatctatgt tggcctcgcg tcgtgcagag | 180 |
| gcggaagctc tgggtgtacc gccagatctg attgaggatg ttttgcgtcg ggtgatgcgt | 240 |
| gaatcttact ccagtgaaaa cgacaaagga tttaaaacac tttgtccgtc actgcgtccg | 300 |
| gtggttatcg tcggcggtgg cggtcagatg ggacgcctgt tcgagaagat gctgaccctc | 360 |
| tcgggttatc aggtgcggat tctggagcaa catgactggg atcgagcggc tgatattgtt | 420 |
| gccgatgccg aatggtgat tgttagtgtg ccaatccacg ttactgagca agttattggc | 480 |
| aaattaccgc ctttaccgaa agattgtatt ctggtcgatc tggcatcagt gaaaaatggg | 540 |
| ccattacagg ccatgctggt ggcgcatgat ggtccggtgc tggggctaca cccgatgttc | 600 |
| ggtccggaca gcgtagcct ggcaaagcaa gttgtggtct ggtgtgatgg acgtaaaccg | 660 |
| gaagcatacc aatggtttct ggagcaaatt caggtctggg gcgctcggct gcatcgtatt | 720 |
| agcgccgtcg agcacgatca gaatatggcg tttattcagg cactgcgcca ctttgctact | 780 |
| tttgcttacg ggctgcacct ggcggaagaa atgttcggc ttgagcaact tctggcgctc | 840 |
| tcttcgccga tttaccgcct tgagctggcg atggtcgggc gactgtttgc tcaggatccg | 900 |
| cagctttatg ccgacatcat tatgtcgtca gagcgtaatc tggcgttaat caaacgttac | 960 |
| tataagcgtt tcggcgaggc gattgagttg ctggagcagg gcgataagca ggcgtttatt | 1020 |
| gacagtttcc gcaaggtgga gcactggttc ggcgattacg cacagcgtct tcagagtgaa | 1080 |
| agccgcgtgt tattgcgtca ggcgaatgac aatcgccagt aa | 1122 |

<210> SEQ ID NO 38
<211> LENGTH: 1122
<212> TYPE: DNA
<213> ORGANISM: Escherichia coli

<400> SEQUENCE: 38

| | |
|---|---|
| atggttgctg aattgaccgc attacgcgat caagttgatg aagtcgataa agcgctgctg | 60 |
| aatttattag cgaagcgtct ggaactggtt gctgaagtgg gcgaggtgaa aagccgcttt | 120 |
| ggactgccta tttatgttcc ggagcgcgag gcatctatgt tggcctcgcg tcgtgcagag | 180 |
| gcggaagctc tgggtgtacc gccagatctg attgaggatg ttttgcgtcg ggtgatgcgt | 240 |
| gaatcttact ccagtgaaaa cgacaaagga tttaaaacac tttgtccgtc actgcgtccg | 300 |
| gtggttatcg tcggcggtgg cggtcagatg ggacgcctgt tcgagaagat gctgaccctc | 360 |
| tcgggttatc aggtgcggat tctggagcaa catgactggg atcgagcggc tgatattgtt | 420 |
| gccgatgccg aatggtgat tgttagtgtg ccaatccacg ttactgagca agttattggc | 480 |
| aaattaccgc ctttaccgaa agattgtatt ctggtcgatc tggcatcagt gaaaaatggg | 540 |
| ccattacagg ccatgctggt ggcgcatgat ggtccggtgc tggggctaca cccgatgttc | 600 |
| ggtccggaca gcgtagcct ggcaaagcaa gttgtggtct ggtgtgatgg acgtaaaccg | 660 |
| gaagcatacc aatggtttct ggagcaaatt caggtctggg gcgctcggct gcatcgtatt | 720 |
| agcgccgtcg agcacgatca gaatatggcg tttattcagg cactgcgcca ctttgctact | 780 |
| tttgcttacg ggctgcatct ggcagaagaa atgttcagc ttgagcaact tctggcgctc | 840 |

```
tcttcgccga tttaccgcct tgagctggcg atggttgggc gactgtttgc tcaggatccg      900
cagctttatg ccgacatcat tatgttgtca gagcgtaatc tggcgttaat caaacgttac      960
tataagcgtt tcggcgaggc gattgagttg ctggagcagg gcgataagca ggcgtttatt     1020
gacagtttcc gcaaggtgga gcactggttc ggcgattacg tacagcgttt tcagagtgaa     1080
agccgcgtgt tattgcgtca ggcgaatgac aatcgccagt aa                        1122
```

<210> SEQ ID NO 39
<211> LENGTH: 1122
<212> TYPE: DNA
<213> ORGANISM: Escherichia coli

<400> SEQUENCE: 39

```
atggttgctg aattgaccgc attacgcgat caaattgatg aagtcgataa agcgctgctg       60
aatttattag cgaagcgtct ggaactggtt gctgaagtgg gcgaggtgaa aagccgcttt      120
ggactgccta tttatgttcc ggagcgcgag gcatctatgt tggcctcgcg tcgtgcagag      180
gcggaagctc tgggtgtacc gccagatctg attgaggatg ttttgcgtcg ggtgatgcgt      240
gaatcttact ccagtgaaaa cgacaaagga tttaaaacac tttgtccgtc actgcgtccg      300
gtggttatcg tcggcggtgg cggtcagatg ggacgcctgt tcgagaagat gctgaccctc      360
tcgggttatc aggtgcggat tctggagcaa catgactggg atcgagcggc tgatattgtt      420
gccgatgccg aatggtgat tgttagtgtg ccaatccacg ttactgagca agttattggc      480
aaattaccgc ctttaccgaa agattgtatt ctggtcgatc tggcatcagt gaaaaatggg      540
ccattacagg ccatgctggt ggcgcatgat ggtccggtgc tggggctaca cccgatgttc      600
ggtccggaca gcggtagcct ggcaaagcaa gttgtggtct ggtgtgatgg acgtaaacca      660
gaagcatacc aatggtttct ggagcaaatt caggtctggg gcgctcggct gcatcgtatt      720
agcgccgtcg agcacgatca gaatatggcg tttattcagg cactgcgcca ctttgctact      780
tttgcttacg ggctgcacct ggcagaagaa aatgttcagc ttgagcaact tctggcgctc      840
tcttcgccga tttaccgcct tgagctggcg atggtcgggc gactgtttgc tcaggatccg      900
cagctttatg ccgacatcat tatgttgtca gagcgtaatc tggcgttaat caaacgttac      960
tataagcgtt tcggcgaggc gattgagttg ctggggcagg gcgataagca ggcgtttatt     1020
gacagtttcc gcaaggtgga gcattggttc ggcgattacg cacagcgtct tcagagtgaa     1080
agccgcgtgt tattgcgtca ggcgaatgac aatcgccagt aa                        1122
```

<210> SEQ ID NO 40
<211> LENGTH: 1122
<212> TYPE: DNA
<213> ORGANISM: Escherichia coli

<400> SEQUENCE: 40

```
atggttgctg aattgaccgc attacgcgat caaattgatg aagtcgataa agcgctgctg       60
aatttattag cgaagcgtct ggaactggtt gctggagtgg gcgaggtgaa aagccgcttt      120
ggactgccta tttatgttcc ggagcgcgag gcatctatgt tggcctcgcg tcgtgcagag      180
gcggaagctc tgggtgtacc gccagatctg attgaggatg ttttgcgtcg ggtgatgcgt      240
gaatcttact ccagtgaaaa cgacaaagga tttaaaacac tttgtccgtc actgcgtccg      300
gtggttatcg tcggcggtgg cggtcagatg ggacgcctgt tcgagaagat gctgaccctc      360
tcgggttatc aggtgcggat tctggagcaa catgactggg atcgagcggc tgatattgtt      420
```

| | |
|---|---|
| gccgatgccg gaatggtgat tgttagtgtg ccaatccacg ttactgagca agttattggc | 480 |
| aaattaccgc ctttaccgaa agattgtatt ctggtcgatc tggcatcagt gaaagatggg | 540 |
| ccattacagg ccatgctggt ggcgcatgat ggtccggtgc tggggctaca cccgatgttc | 600 |
| ggtccggaca gcggtagcct ggcaaagcaa gttgtggtct ggtgtgatgg acgtaaaccg | 660 |
| gaagcatacc aatggtttct ggagcaaatt caggtctggg gcgctcggct gcatcgtatt | 720 |
| agcgccgtcg agcacgatca gaatatggcg tttattcagg cactgcgcca ctttgctact | 780 |
| tttgcttacg gctgcacct ggcagaagaa aatgttcagc ttgagcaact tctggcgctc | 840 |
| ttttcgccga tttaccgcct tgagctgcg atggtcgggc gactgtttgc tcaggatccg | 900 |
| cagctttatg ccgacatcat tatgtcgtca gagcgtaatc tggcgttaat caaacgttac | 960 |
| tataagcgtt tcggcgaggc gattgagttg ctggagcagg gcgataagca ggcgtttatt | 1020 |
| gacagttttcc gcaaggtgga gcactggttc ggcgattacg cacagcgtct tcagagtgaa | 1080 |
| agccgcgtgt tattgcgtca ggcgaatgac aatcgccagt aa | 1122 |

<210> SEQ ID NO 41
<211> LENGTH: 1122
<212> TYPE: DNA
<213> ORGANISM: Escherichia coli

<400> SEQUENCE: 41

| | |
|---|---|
| atggttgctg aattgaccgc attacgcgat caaattgatg aagtcgataa agcgctgctg | 60 |
| aatttattag cgaagcgtct ggaactggtt gctgaagtgg gcgaggtgaa aagccgcttt | 120 |
| ggactgccta tttatgttcc ggagcgcgag gcatctatgt tggcctcgcg tcgtgcagag | 180 |
| gcggaagctc tgggtgtacc gccagatctg attgaggatg ttttgcgtcg ggtgatgcgt | 240 |
| gaatcttact ccagtgaaaa cgacaaagga tttaaaacac tttgtccgtc actgcgtccg | 300 |
| gtggttatcg tcggcggtgg cggtcagatg ggacgcctgt cgagaagat gctgaccctc | 360 |
| tcgggttatc aggtgcggat ctggagcaa catgactggg atcgagcggc tgatattgtt | 420 |
| gccgatgccg gaatggtgat tgttagtgtg ccaatccacg ttactgagca agttattggc | 480 |
| aaattaccgc ctttaccgaa agattgtatt ctggtcgatc tggcatcagt gaaagatggg | 540 |
| ccattacagg ccatgctggt ggcgcatgat ggtccggtgc tggggctaca cccgatgttc | 600 |
| ggtccggaca gcggtagcct ggcaaagcaa gttgtggtct ggtgtgatgg acgtaaaccg | 660 |
| gaagcatacc aatggtttct ggagcaaatt caggtctggg gcgctcggct gcatcgtatt | 720 |
| agcgccgtcg agcacgatca gaatatggcg tttattcagg cactgcgcca ctttgctact | 780 |
| tttgcttacg gctgcacct ggcagaagaa aatgttcagc ttgagcaact tctggcgctc | 840 |
| tcttcgctga tttaccgcct tgagctgcg atggtcgggc gactgtttgc tcaggatccg | 900 |
| cagctttatg ccgacatcat tatgttgtca gagcgtaatc tggcgttaat caaacgttag | 960 |
| tataagcgtt tcggcgaggc gattgagttg ctggggcagg gcgataagca ggcgtttatt | 1020 |
| gacagttttcc gcaaggtgga gcattggttc ggcgattacg cacggcgttt tcagagtgaa | 1080 |
| agccgcgtgt tattgcgtca ggcgaatgac aatcgccagt aa | 1122 |

<210> SEQ ID NO 42
<211> LENGTH: 1122
<212> TYPE: DNA
<213> ORGANISM: Escherichia coli

<400> SEQUENCE: 42

| | |
|---|---|
| atggttgctg aattgaccgc attacgcgat caaattgatg aagtcgataa agcgctgctg | 60 |

```
aatttattag cgaagcgtct ggaactggtt gctgaagtgg gcgaggtgaa aagccgcttt      120
ggactgccta tttatgttcc ggagcgcgag gcatctatat tggcctcgcg tcgtgcagag      180
gcggaagctc tgggtgtacc gccagatctg attgaggatg ttttgcgtcg ggtgacgcgt      240
gaatcttact ccagtgaaaa cgacaaagga tttaaaacac tttgtccgtc actgcgtccg      300
gtggttatcg tcggcggtgg cggtcagatg ggacgcctgt tcgagaagat gctgaccctc      360
tcgggttatc aggtgcggat tctggagcaa catgactggg atcgagcggc tgatattgtt      420
gctgatgccg gaatggtgat tgttagtgtg ccaatccacg ttactgagca agttattggc      480
aaattaccgc ctttaccgaa agattgtatt ctggtcgatc tggcatcagt gaaaaatggg      540
ccattacagg ccatgctggt ggcgcatgat ggtccggtgc tggggctaca cccgatgttc      600
ggtccggaca gcggtagcct ggcaaagcaa gttgtggtct ggtgtgatgg acgtaaaccg      660
gaagcatacc aatggtttct ggagcaaatt caggtctggg gcgctcgact gcatcgtatt      720
agcgccgtcg agcacgatca gaatatggcg tttattcagg cactgcgcca ctttgctact      780
tttgcttacg ggctgcacct ggcagaagaa aatgttcagc ttgagcaact tctggcgctc      840
tcttcgccga tttaccgcct tgagctggcg atggtcgggc gactgtttgc tcaggatccg      900
cagctttatg ccgacatcat tatgtcgtca gagcgtaatc tggcgttaat caaacgttac      960
cataagcgtt tcggcgaggc gattgagttg ctggagcagg cgataagca ggcgtttatt     1020 gacagtttcc gcaaggtgga gcactggttc ggcgattacg cacagcgttt tcagagtgaa     1080
agccgcgtgt tattgcgtca ggcgaatgac aatcgccagt aa                        1122

<210> SEQ ID NO 43
<211> LENGTH: 33
<212> TYPE: DNA
<213> ORGANISM: Escherichia coli

<400> SEQUENCE: 43
ccggtaccat ggttgctgaa ttgaccgcat tac                                    33

<210> SEQ ID NO 44
<211> LENGTH: 33
<212> TYPE: DNA
<213> ORGANISM: Escherichia coli

<400> SEQUENCE: 44
ccacgcgttt attactggcg attgtcattc gcc                                    33

<210> SEQ ID NO 45
<211> LENGTH: 40
<212> TYPE: DNA
<213> ORGANISM: Escherichia coli

<400> SEQUENCE: 45
ggtattgagg gtcgcatggt tgctgaattg accgcattac                             40

<210> SEQ ID NO 46
<211> LENGTH: 42
<212> TYPE: DNA
<213> ORGANISM: Escherichia coli

<400> SEQUENCE: 46
agaggagagt tagagcctta ttactggcga ttgtcattcg cc                          42

<210> SEQ ID NO 47
```

```
<211> LENGTH: 20
<212> TYPE: DNA
<213> ORGANISM: Escherichia coli

<400> SEQUENCE: 47
taatacgact cactataggg                                               20

<210> SEQ ID NO 48
<211> LENGTH: 19
<212> TYPE: DNA
<213> ORGANISM: Escherichia coli

<400> SEQUENCE: 48
gctagttatt gctcagcgg                                                19

<210> SEQ ID NO 49
<211> LENGTH: 20
<212> TYPE: DNA
<213> ORGANISM: Escherichia coli

<400> SEQUENCE: 49
actgcgtccg gtggttatcg                                               20

<210> SEQ ID NO 50
<211> LENGTH: 20
<212> TYPE: DNA
<213> ORGANISM: Escherichia coli

<400> SEQUENCE: 50
ggcgaagaga gcgccagaag                                               20
```